US012011546B2

(12) United States Patent
Lurie et al.

(10) Patent No.: US 12,011,546 B2
(45) Date of Patent: *Jun. 18, 2024

(54) INSPIRATORY RESISTOR VALVE SYSTEM WITH EXPIRATORY PORT

(71) Applicant: VitaLinC LLC, Minneapolis, MN (US)

(72) Inventors: Keith G. Lurie, Minneapolis, MN (US); Tom Wilmering, Eldorado Springs, CO (US)

(73) Assignee: VitaLinC LLC, Minneapolis, MN (US)

( * ) Notice: Subject to any disclaimer, the term of this patent is extended or adjusted under 35 U.S.C. 154(b) by 367 days.

This patent is subject to a terminal disclaimer.

(21) Appl. No.: 17/412,784

(22) Filed: Aug. 26, 2021

(65) Prior Publication Data

US 2021/0386961 A1 Dec. 16, 2021

Related U.S. Application Data

(63) Continuation of application No. 17/207,983, filed on Mar. 22, 2021, now Pat. No. 11,103,672.

(60) Provisional application No. 62/992,706, filed on Mar. 20, 2020.

(51) Int. Cl.
*A61M 16/20* (2006.01)
*A61M 16/08* (2006.01)
*A61M 16/10* (2006.01)

(52) U.S. Cl.
CPC ........ *A61M 16/20* (2013.01); *A61M 16/0816* (2013.01); *A61M 16/1065* (2014.02); *A61M 16/208* (2013.01); *A61M 2205/3584* (2013.01); *A61M 2230/00* (2013.01)

(58) Field of Classification Search
CPC .............. A61M 16/00; A61M 16/0048; A61M 16/0078; A61M 16/0084; A61M 16/06; A61M 16/0816; A61M 16/0866; A61M 16/1065; A61M 16/20; A61M 16/208
See application file for complete search history.

(56) References Cited

U.S. PATENT DOCUMENTS

| 3,556,122 | A | 1/1971 | Laerdal |
| 4,856,548 | A | 8/1989 | Paluch |
| 6,062,219 | A | 5/2000 | Lurie et al. |
| 11,103,672 | B1 | 8/2021 | Lurie et al. |

(Continued)

FOREIGN PATENT DOCUMENTS

WO 2021-189033 A1 9/2021

OTHER PUBLICATIONS

Non-Final Office Action dated May 28, 2021 in U.S. Appl. No. 17/207,983, 17 pages.

(Continued)

*Primary Examiner* — Joseph D. Boecker
(74) *Attorney, Agent, or Firm* — Kilpatrick Townsend & Stockton LLP

(57) ABSTRACT

An inspiratory resistor valve system (IRV) to regulate intrathoracic pressure during positive pressure breathing, spontaneous inspirations, and CPR may include an inspiratory port. The IRV system may include patient port. The IRV system may include a separate expiratory port. The IRV may include a plurality of atmospheric pressure sensitive valves. The plurality of atmospheric pressure sensitive valves may isolate the expiratory port and the inspiratory port from one another.

18 Claims, 20 Drawing Sheets

(56) References Cited

U.S. PATENT DOCUMENTS

| | | | |
|---|---|---|---|
| 2003/0062040 A1* | 4/2003 | Lurie | A61M 16/208 |
| | | | 128/202.28 |
| 2003/0192547 A1* | 10/2003 | Lurie | A61M 16/0084 |
| | | | 128/207.12 |
| 2009/0020128 A1* | 1/2009 | Metzger | A61M 16/208 |
| | | | 128/207.16 |
| 2009/0260628 A1* | 10/2009 | Flynn, Sr. | A61M 16/1065 |
| | | | 128/203.29 |
| 2010/0095965 A1 | 4/2010 | Piper | |
| 2011/0132359 A1 | 6/2011 | Poree | |
| 2014/0005566 A1 | 1/2014 | Homuth et al. | |
| 2014/0144447 A1* | 5/2014 | Kuypers | A61M 16/0072 |
| | | | 128/205.24 |
| 2021/0290888 A1* | 9/2021 | Lurie | A61M 16/0009 |

OTHER PUBLICATIONS

Notice of Allowance dated Jun. 30, 2021 in U.S. Appl. No. 17/207,983, 10 pages.

International Search Report and Written Opinion dated Jul. 23, 2021 in International Patent Application No. PCT/US2021/023402, 12 pages.

\* cited by examiner

INSPIRATORY RESISTOR VALVE SYSTEM WITH EXPIRATORY PORT

CROSS-REFERENCE TO RELATED APPLICATIONS

This application is a continuation of U.S. patent application Ser. No. 17/207,983, filed Mar. 22, 2021, which claims priority to U.S. Provisional Patent Application No. 62/992,706, filed Mar. 20, 2020, the disclosure of which is incorporated by reference herein in its entirety.

BACKGROUND OF THE INVENTION

Devices are often used to regulate a patient's intrathoracic pressure during the performance of cardiopulmonary resuscitation (CPR) and/or other medical treatments. Some techniques involve the use of a valve structure, called an impedance threshold device (ITD), to periodically prevent or impede the flow in respiratory gases into the lungs, which helps generate a negative pressure within the patient's thorax. Once a certain negative intrathoracic pressure is reached, the valve opens, allowing respiratory oxygen to enter the patient's lungs. During CPR, positive pressure breaths are periodically delivered through the ITD to periodically inflate the lungs and deliver oxygen. While conventional devices effectively provide increased negative pressure levels, problems can arise when fluid from the patient, such as that caused by pulmonary edema, passes from the patient's airway and into the valve or other device, thereby making them less effective or ineffective. Further, expiratory gases mix with inspiratory gases in conventional ITDs. Improvements in intrathoracic pressure regulation are therefore desired.

BRIEF SUMMARY OF THE INVENTION

Embodiments of the present invention are directed to devices that increase the blood flow to a patient's chest during the recoil phase of CPR and during spontaneous respiration. In particular, embodiments are directed to inspiratory resistor valve systems with expiratory ports (IRVs) that have an inspiratory port and a separate expiratory port to prevent expiratory gases from being mixed with inspiratory gases, thus separating inflow from outflow and allowing for the delivery of higher concentrations of $O_2$ to the patient during CPR. Additionally, embodiments provide an exit flow path for any fluids, such as those resulting from pulmonary edema, that directs such fluids out of the IRV and away from the inspiratory flow path of the IRV. In this regard backflow protection can be desirable to help maintain the integrity of fluid sensitive valving mechanisms. In some embodiments expiratory gases pass through a filter contiguous with the expiratory port to protect rescue personnel from potential pathogens, including viral particles. In some embodiments one or more sensors are located within the IRV and between the inspiratory and expiratory flow ports.

In one embodiment, an inspiratory resistor valve system (IRV) to regulate intrathoracic pressure during positive pressure breathing, spontaneous inspirations, and CPR is provided. The IRV may include an inspiratory port, a patient port, a separate expiratory port, and a plurality of atmospheric pressure sensitive valves. The plurality of atmospheric pressure sensitive valves may isolate the expiratory port and the inspiratory port from one another.

In some embodiments, the plurality of atmospheric pressure sensitive valves may be concentrically arranged. The plurality of atmospheric pressure sensitive valves may occlude the expiratory port during positive pressure breath delivery and occlude the inspiratory port and open the expiratory port to enable egress of respiratory gases from a patient's during expiration or chest compressions. All of the plurality of atmospheric pressure sensitive valves in regions of the inspiratory port and the expiratory port may remain in a closed position until a pressure within the patient port is between −5 and −20 cm of water. One or both of a filter interfaced with the expiratory port and one valve of the plurality of atmospheric pressure sensitive valves may provide between 2 and 10 cm of water of expiratory resistance. Each of the plurality of atmospheric pressure sensitive valves may include one-way valves selected from a group comprising: a duckbill valve, a ball valve, an annular valve, a circular valve, a butterfly valve, a check valve, a balloon valve, a mushroom valve, a fish mouth valve, and a disk valve. The patient port may include a non-rebreather valve that enables substantially resistance-free positive pressure ventilation from the inspiratory port to the patient port.

In another embodiment, an inspiratory resistor valve system (IRV) may include a housing having an upper region, a lower region, and an expiratory region. The IRV may include a first pressure-responsive one-way valve disposed between the upper region and the lower region for allowing for positive pressure ventilation with less than 5 cm H2O resistance and for preventing all respiratory gases from flowing from the upper region to the lower region when a pressure in the lower region is sub-atmospheric. The IRV may include a second pressure-responsive valve disposed between the upper region and the lower region that remains closed until the pressure in the lower region falls below a threshold level, causing the second pressure responsive valve to open to allow the respiratory gases to flow to the patient's lungs due to a pressure differential between atmospheric pressure and the pressure in the lower region. The IRV may include a third pressure-responsive valve disposed between the upper region and the expiratory region for preventing all expiratory fluids from flowing to the upper region when the pressure in the thorax is greater than atmospheric pressure. The IRV may include a fourth pressure-responsive valve in the expiratory region that occludes when pressure in the lower region interfacing with the patient is below atmospheric pressure and opens when pressure in the lower region interfacing with the patient is above atmospheric pressure.

In some embodiments, the threshold level may be between about −5 and −20 cm of water. The IRV may include a physiological sensor disposed within one or both of the upper region and the lower region. The IRV may include a communications interface that transmits signals from the physiological sensor to one or both of a ventilation device and a compression device. The IRV may include a filter interfaced with the expiratory region. The second pressure-responsive valve may include a duck-bill valve having an outer surface that selectively engages a valve seat. The duck-bill valve may open to enable inspiratory flow to be delivered to the patient while the outer surface engages the valve seat to occlude the expiratory region from the upper region. The duck-bill valve may close and the outer surface may move away from the valve seat to expel the expiratory fluids from the IRV and to prevent the expiratory fluids from flowing to the upper region.

In another embodiment, an inspiratory resistor valve system (IRV) may include a housing, a ventilation port that is configured to interface with a ventilation device, and a patient port that is configured to interface with a patient interface device. The IRV may include a separate expiration port and a positive pressure ventilation flow path that is in fluid communication with the ventilation port and the patient port. The positive pressure ventilation flow path may be configured to direct respiratory air from the ventilation port to the patient port. The IRV may include a patient inspiration flow path that is in fluid communication with the patient port. The patient inspiration flow path may be configured to deliver air to the patient port in the event of spontaneous inspiration of a patient. The IRV may include an expiration flow path that is in fluid communication with the patient port. The expiration flow path may be configured to direct expiratory fluids from the patient out of the IRV via the expiration port. The expiration flow path may be separated from at least a portion of the positive pressure ventilation flow path and the patient inspiration flow path via a series of pressure-responsive valves to separate inflow from outflow such that expiratory fluids are not mixed with inspiratory gases, thus resulting in delivery of higher concentrations of $O_2$ to the patient during CPR.

In some embodiments, the series of pressure-responsive valves may include a first atmospheric pressure valve interfaced with the positive pressure ventilation flow path, a first pressure-sensitive valve interfaced with the patient inspiration flow path, a second pressure-sensitive valve interfaced between the inspiration flow path and the expiration flow path, and a second atmospheric pressure valve that is disposed within the expiration port. A closing pressure of the first atmospheric pressure valve may be less than −1 cm H2O. An opening pressure of the first pressure-sensitive valve may be between about −5 and −20 cm H2O. The second pressure-sensitive valve may open when the pressure in the ventilation flow path is greater than 0 cm H2O and may close when expiration flow path pressure is greater than 0 cm H2O. An opening pressure of the second atmospheric pressure valve may be between about 0 and 10 cm H2O. A closing pressure of the of the second atmospheric pressure valve may be less than −1 cm H2O. The second pressure-sensitive valve and the second atmospheric pressure valve may form a single non-rebreather valve. The second atmospheric pressure valve may enable respiratory fluids to enter the patient but prevents the respiratory fluids from the lungs from contact with the first atmospheric pressure valve. The IRV may include a first diaphragm coupled with a top surface of the positive pressure ventilation flow path. The IRV may include a second diaphragm coupled with the lower surface of the expiration flow path. The first diaphragm and the second diaphragm may each have a cracking pressure that is substantially at atmospheric pressure.

During delivery of positive pressure ventilations, the first atmospheric pressure valve and the second atmospheric pressure valve may open while the first pressure-sensitive valve and the second pressure-sensitive valve may be closed. During spontaneous inspiration, the first pressure-sensitive valve and the second atmospheric pressure valve may be open, while the first atmospheric pressure valve and the second pressure-sensitive valve may be closed. During one or both of a chest compression phase of CPR and a patient expiration, the second pressure-sensitive valve may be open while the first atmospheric pressure valve, the first pressure-sensitive valve, and the second atmospheric pressure valve may be closed, thereby enabling respiratory fluids to exit the IRV without mixing with inspiratory gases. During a decompression phase of CPR, the first atmospheric pressure valve, the first pressure-sensitive valve, and the second pressure-sensitive valve may be closed, thereby lowering intrathoracic pressure and preventing respiratory gases from entering the patient and providing room for increased blood volume to return to the patient's heart during the decompression phase to increase circulation to the patient's coronary arteries and lower intracranial pressure.

BRIEF DESCRIPTION OF THE DRAWINGS

A further understanding of the nature and advantages of various IRV embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

Figure 1A:
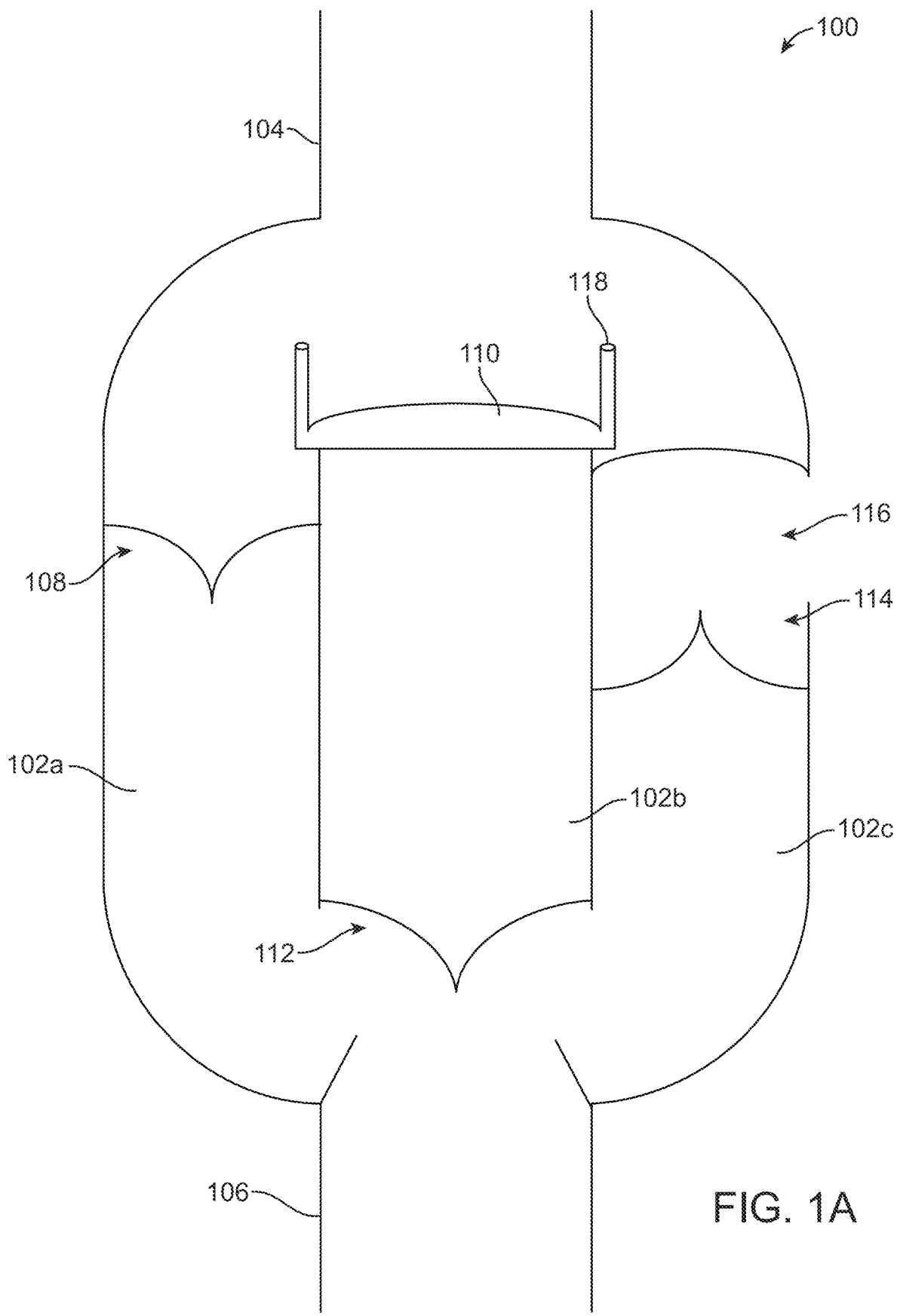
FIG. 1A illustrates a schematic of an inspiratory resistor valve system with an expiratory port (IRV) according to embodiments.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Performance of CPR on patients in cardiac arrest includes chest compressions (performed manually and/or using an automated device) in order to assist in the circulation of blood to the vital organs including the heart, lungs, and brain. In some embodiments, active compression decompression (ACD) CPR may be performed, which involves actively decompressing between each compression, rather allowing the chest to recoil on its own. During the compression phase of CPR, blood is pushed out of the heart into the aorta and air is pushed out of the thorax and into the atmosphere via the trachea and airways. During the decompression phase (both passive and active), blood from areas remote from the thorax is drawn into the thorax and air is drawn into the thorax via the patient's airways.

Application of the methods and devices described in this application, in conjunction with any of the methods of CPR noted above, result in an intrathoracic vacuum during the chest wall recoil phase. This increases circulation to the coronary arteries and lowers intracranial pressure during the chest wall decompression phase. Oftentimes, a positive pressure ventilation needs to be delivered to the patient periodically to inflate the lungs and provide oxygen. The lungs can also be inflated by periodic negative pressure ventilation with, for example, an iron lung or chest cuirass device.

During the chest decompression or recoil phase of CPR, or during spontaneous inspiration, pressures within the thorax decrease to pressure levels between −1 to −15 cm H2O. This draws respiratory gases into the lungs unless there is an IRV within the circuit. An IRV impedes respirator gases from entering into the lungs because of the valve system. With recoil of the chest, either passive or active, or patient inspiration, when an IRV is in the circuit the negative intrathoracic pressure generated during the chest recoil phase of CPR or during a spontaneous inspiration produces a vacuum that enhances venous blood flow back into the lungs and lowers intracranial pressure. This collectively increases cardiac preload and increases cardiac outcome both during CPR and spontaneous breathing. During CPR this process occurs faster with active decompression of the chest during the chest recoil or decompression phase of CPR. It also occurs more efficiently with elevation of the head and thorax during CPR or in the setting or traumatic brain injury: elevation of the head and thorax harnesses gravity to help drain venous blood from the brain and it improves the distribution of blood within the lungs.

During chest compressions, blood is propelled out of the heart to the brain and the rest of the body and the air is expelled from the lungs. Air may be expelled through an IRV that can provide a low level of fixed or variable resistance, typically in the range of about 0 cm H2O to about 15 cm H2O, more commonly about 2 cm H2O to about 10 cm H2O. This resistance may be adjustable and may be provided by one or more valves of an IRV system (such as an expiratory valve as described herein), a filter material, and/or other means having a low flow of positive pressure gases, such as oxygen.

With each chest compression air is pushed out of the lungs, and not allowed back into the lungs because of the valve system. This results in a progressive decrease in respiratory gases within the lungs. The volume of respiratory gas that is expelled from the lungs with each chest compression creates space that is filled by more blood returning to the heart and lungs during the decompression phase whenever a positive pressure is not being applied to the thorax by chest compressions. This process occurs faster with active decompression of the chest during the chest recoil or decompression phase of CPR. To help generate even more negative pressure within the patient's thorax between chest compressions (during the decompression phase), a valve structure in accordance with the present invention may be interfaced with the patient's airway. Such valve structures may periodically prevent or impede the flow in respiratory gases into the lungs while permitting respiratory gases to escape from the lungs during chest compressions, while permitting periodic ventilation.

FIG. 1A illustrates a schematic of a valve structure in the form of an inspiratory resistor valve with expiratory port (IRV) 100. IRV 100 may include a number of valves that operate to regulate intrathoracic pressure of a patient. IRV 100 may include a number of branches, tubes, and/or other lumens 102 that enable respiratory gases to flow to and from the patient. As illustrated, the IRV 100 includes patient inspiration lumen 102a, a positive pressure ventilation lumen 102b, and a patient expiration lumen 102c (although other configurations are possible). Here, the lumens 102 are coupled to one another in parallel, with a ventilation port 104 disposed at a top end of the lumens 102 and a patient port 106 disposed at a bottom end of the lumens 102, however other arrangements of the lumens 102 and/or ports are possible. Various one-way valves may be provided within one or more of the lumen 102 to control the flow of respiratory gases to and from the patient. The one-way valves may be in the form of check valves, fish mouth valves, spring valves, duck valves, ball valves, and/or other mechanical or electronically controlled valves and switches.

As illustrated, the patient inspiration lumen 102a includes one-way valve 108 that operates as a safety valve to enable respiratory gases to be drawn into the patient's airway via the ventilation port 104 in the event of spontaneous inspiration by the patient, while preventing gases from flowing outward from the IRV 100. Oftentimes, the one-way valve 108 has a cracking pressure of between about −5 and −20 cm H2O.

The positive pressure lumen 102b is configured to enable positive pressure ventilations to be delivered to the patient's airway. The positive pressure lumen 102b includes a moveable and/or deformable diaphragm 110 that seals a top end of the positive pressure lumen 102b. The positive pressure lumen 102b also include a one-way valve 112 that permits air to pass into the patient port 106 and subsequently delivered to the patient's airways. One-way valve 112 also prevents the backward flow of respiratory gases and/or other fluids from the lungs (e.g., pulmonary edema fluid and/or blood) into the positive pressure lumen 102b. In some embodiments, the diaphragm 110 may have a cracking pressure that is substantially equal to atmospheric pressure such that positive pressure respirations may move and/or deform the diaphragm 110 such that the positive pressure air may be delivered to an interior of the positive pressure lumen 102b. In some embodiments, to provide a diaphragm 110 that has a cracking pressure that is substantially equal to atmospheric pressure, the diaphragm 110 may include one or more ventilation ports 118 that enable airflow attributed to the movement of the diaphragm 110 to pass through to minimize any air resistance associated with the moving diaphragm 110. Once past the diaphragm 110, the incoming positive pressure airflow then forces the one-way valve 112 open and passes into the patient's airways. The one-way valve 112 may have a cracking pressure that is less than 1 cm H2O, and possibly 0 cm H2O such that any amount of positive pressure respiration may cause the one-way valve 112 to open. By designing the diaphragm 110 and the one-way valve 112 to have low cracking or opening pressures, the respiratory gases pass through the IRV 100 and into the patient's airways with minimal or no resistance from the IRV 100.

The expiration lumen 102c is configured to enable expiratory gases and/or other fluids from the patient to be evacuated out of the IRV 100. To do so, the expiration lumen 102 includes a one-way valve 114 that leads to an expiratory port 116. A top of the expiration lumen 102c may be sealed from the ventilation port 104 so as to prevent any expiratory gases or other fluids from passing through the ventilation port 104. The one-way valve 114 has a cracking pressure of between about 0 and 12 mmHg. This enables the one-way valve 114 to open when fluids (gas and/or liquids) are expelled from the patient's airways, thereby allowing the fluids to exit the IRV 100 via the expiratory port 116. One-way valve 114 may also have a fixed or variable resistance that is adjustable over a range of expiratory pressures between 2-12 mmHg. Delivery of chest compressions during CPR forces air out of the patient's lungs. This air may pass through the one-way valve 114 and out the expiratory port 116. Similarly, patient expiration may flow through the one-way valve 114 and out the expiratory port 116. In some embodiments, pulmonary edema may occur, causing fluids that may get expired by the patient and delivered into the IRV 100 via the patient port 106. These fluids may also pass through the one-way valve 114 and out the expiratory port. In some embodiments a filter, such as a HEPA filter, may be attached to or incorporated into the interface between the expiratory port and the atmosphere. This may serve to prevent harmful germ particles (bacterial and viral) from contaminating the air around the patient, thus protecting rescuers from possible infection. The filter may also be used as an intentional means to provide a level of expiratory resistance.

Figure 1B:
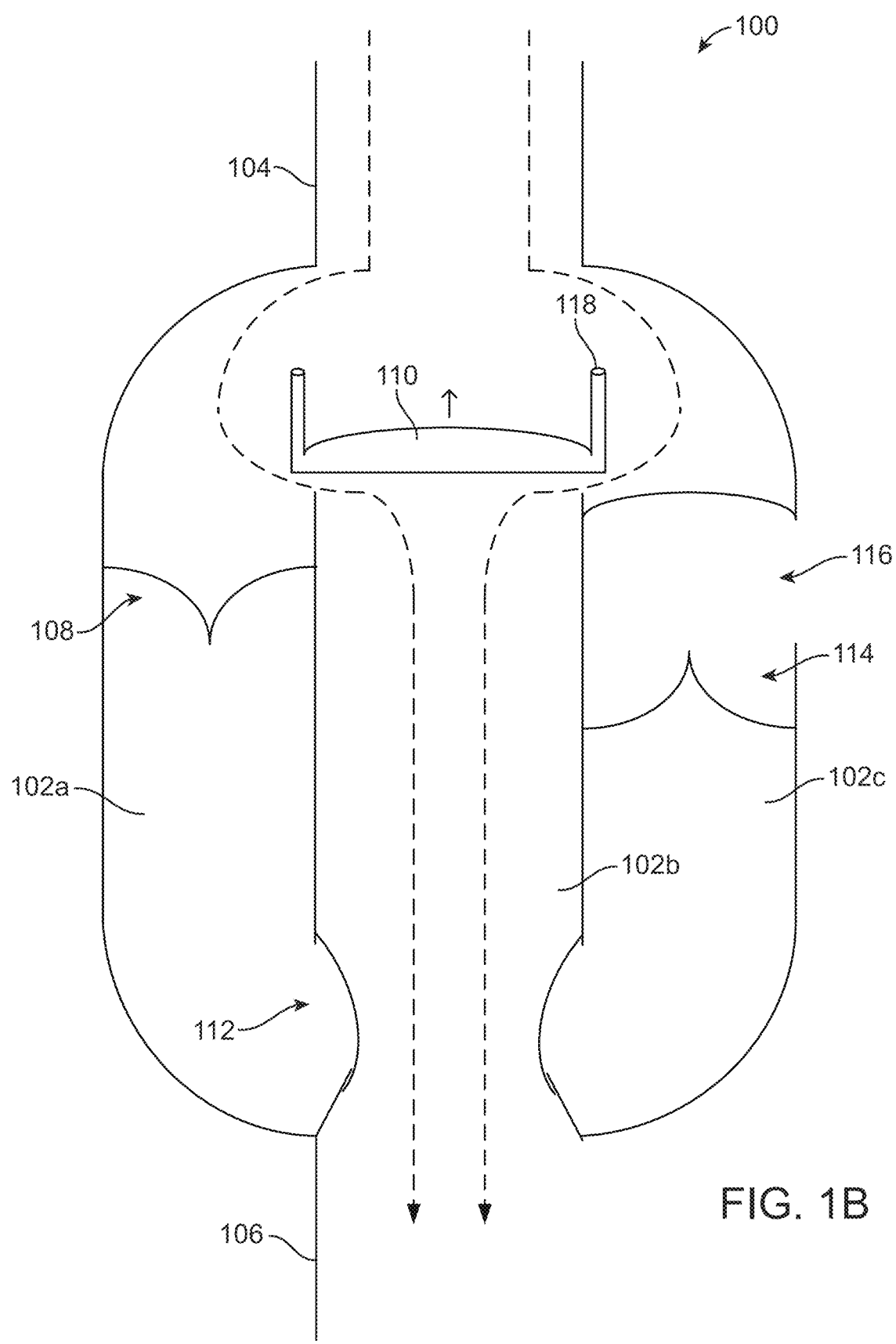
FIG. 1B illustrates airflow through the IRV of FIG. 1A during delivery of a positive pressure ventilation.

FIGS. 1B-1E illustrate the operation of the IRV 100 under different respiration conditions. In particular, these figures detail positions of the various valves of the IRV 100 throughout respiration and CPR. The arrows in FIG. 1B illustrate airflow through the IRV 100 during delivery of a positive pressure ventilation. Positive pressure ventilations may be delivered using a manual and/or automated respirator that is coupled with the ventilation port 104. For example, ventilations may be delivered using mouth-mouth ventilation, a mouth-mask, a resuscitator bag, an automatic or semi-automatic ventilator, a body cuirass or iron lung like device and/or the like. During ventilation, air is typically forced into the IRV 100 via the ventilation port 104 at a pressure that is below the cracking pressure of the one-way valve 108 (e.g. at less than 5-12 cm H2O). In the case that the air pressure of the positive pressure respiration is below the cracking pressure of the one-way valve 108, the positive pressure respiration cannot pass through the one-way valve 108 and instead flows against an underside of the diaphragm 110. This air pressure causes the diaphragm 110 to move and/or deform to allow the airflow to enter the positive pressure lumen 102b. The air then forces open the one-way valve 112 and is delivered to the patient's airway via the patient port 106. During positive pressure ventilations, the one-way valves 108 and 114 remain closed, such that all air delivered by the respirator is delivered to the patient. In some embodiments, one-way valve 112, which could be a duck bill or fish mouth valve, closes off expiratory lumen 102c preventing the positive pressure breath from opening one-way valve 114. In such configurations one-way valve 112 serves two functions in the IRV 100 with a separate expiratory port 116: 1) to prevent backflow of gases and fluids from the lungs and 2) to occlude the expiratory port structure during a positive pressure ventilation.

Figure 1C:
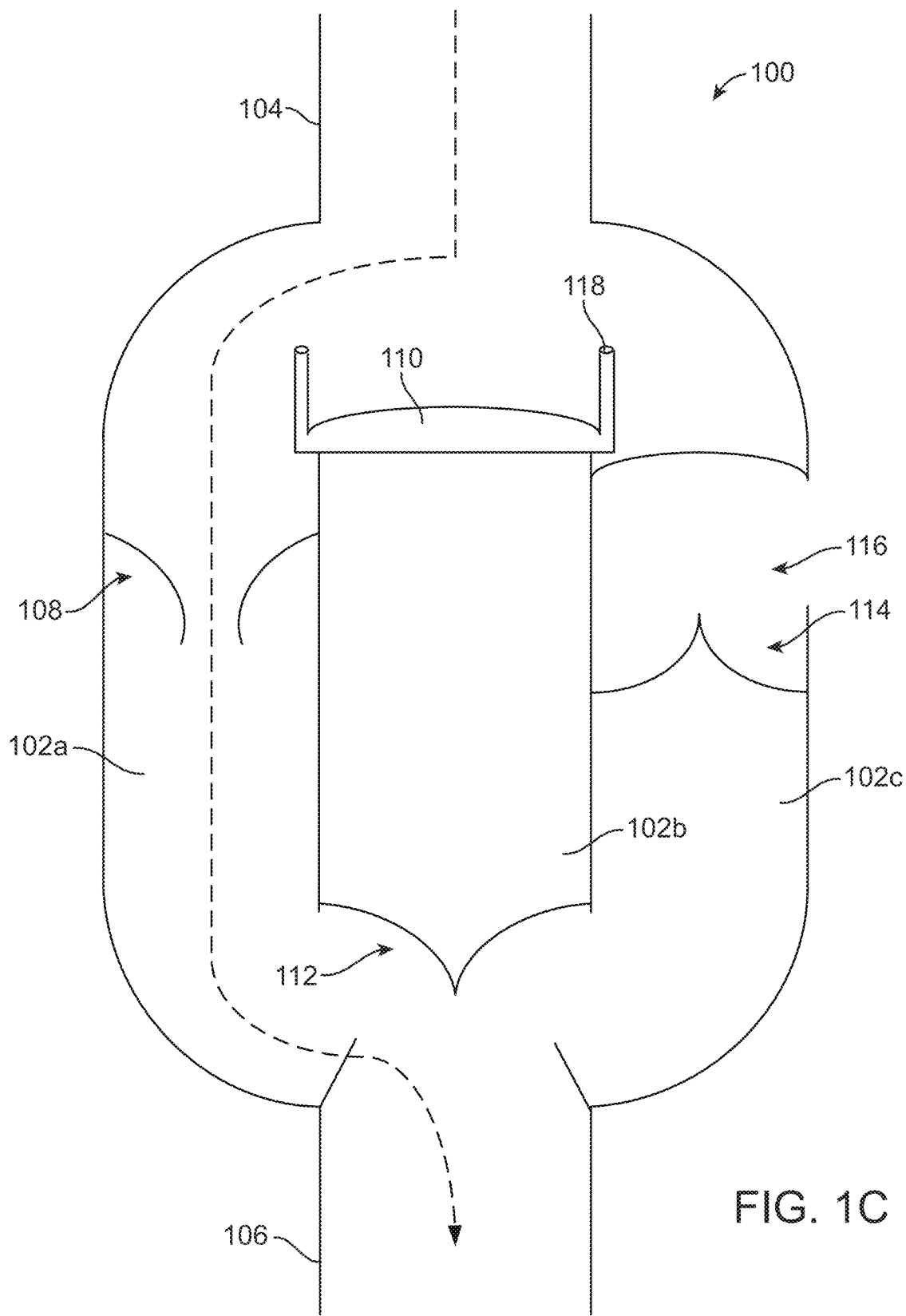
FIG. 1C illustrates airflow through the IRV of FIG. 1A during spontaneous inspiration.

In some cases, the patient may spontaneously inspire, creating a negative pressure within the chest that causes air to be drawn into the patient port 106 as demonstrated by the arrow in FIG. 1C. As the air is being drawn in, rather than pushed in, the diaphragm 110 is drawn against the top surface of the positive pressure lumen 102b, thereby sealing the positive pressure lumen 102b and preventing air from passing through. Simultaneously, one-way valve 114 closes, such that both diaphragm 110 and one-way valve close when the pressure within the patient port 106 is less than 1 atmosphere. When the force of the patient's inspiration exceeds the cracking pressure of the one-way valve 108, the one-way valve 108 opens and respiratory gases are drawn into the patient's airways via the patient inspiration lumen 102a and patient port 106 as illustrated here. Although the one-way valve 108 opens at a predetermined cracking or opening pressure, diaphragm 110 and one-way valve 114 remain closed as long as the pressure in the patient port 106 remains less than 1 atmosphere. For example, during spontaneous inspiration or during chest wall recoil after a compression during CPR, the negative pressure within the chest maintains the diaphragm 110 and one-way valve 114 in a closed position. During spontaneous patient inspiration, the negative pressure generated within the chest prior to valve 108 opening pulls venous blood from the brain and other structures outside the thorax back into the thorax. This increases cardiac output, blood circulation throughout the body, and blood pressure. The cracking pressure on valve 108 may vary between 5-20 cm H2O depending upon the clinical need. Typically during CPR the cracking pressure that provides optimal clinical benefit is around 10-16 cm H2O. Within this range circulation is enhanced.

Figure 1D:
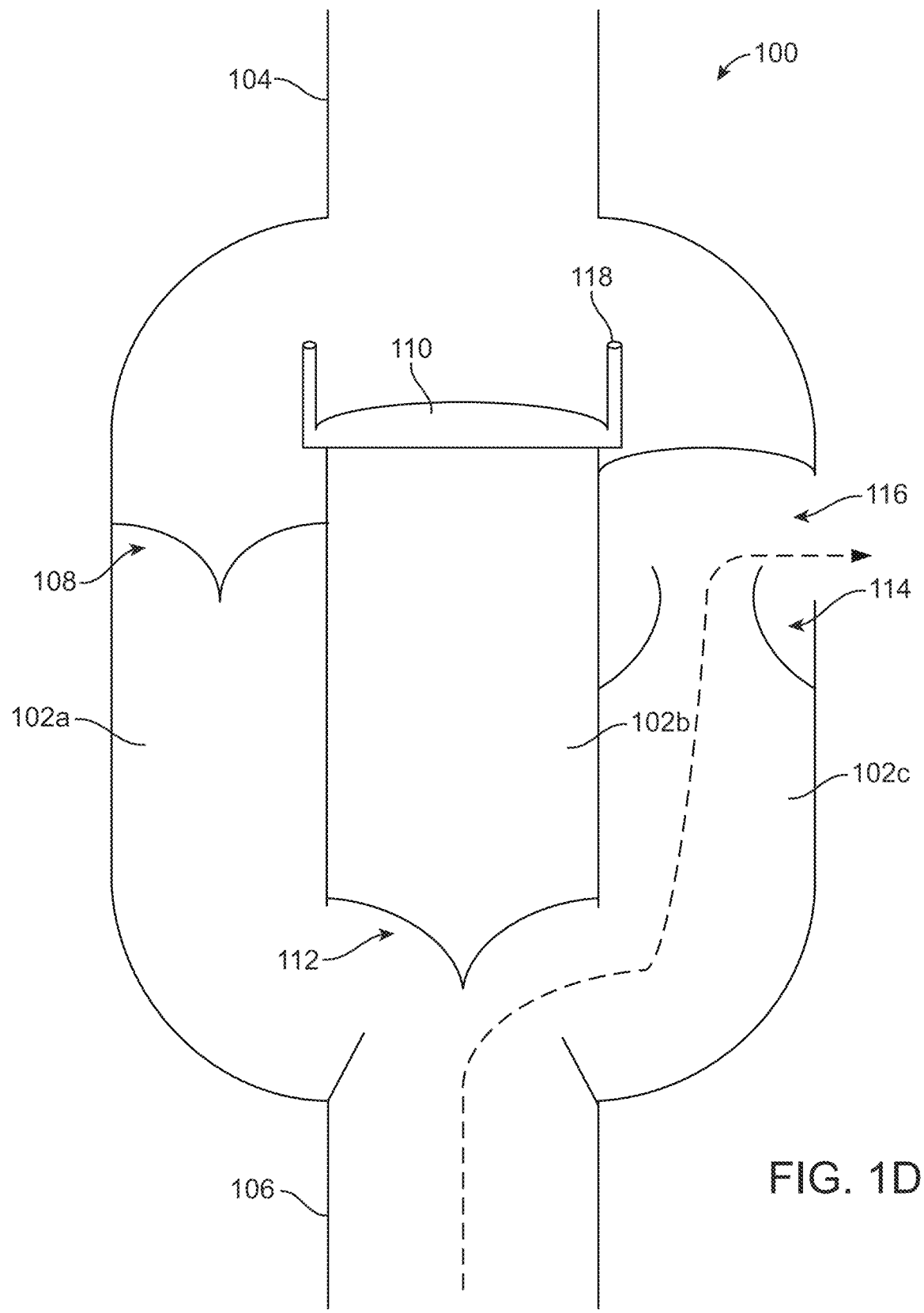
FIG. 1D illustrates airflow through the IRV of FIG. 1A during a chest compression phase of CPR or a patient expiration.

When the chest is compressed (manually and/or automatically) and/or the patient expires, respiratory gases flow from the patient and out through the IRV 100 as shown by the arrow in FIG. 1D. For example, expiratory gases pass through the patient port 106 and force the one-way valve 114 to open. The expiratory gases then flow through the one-way valve 114 and out the expiratory port 116. Due to the direction of operation of the one-way valves 108 and 112, these valves 108, 112 are both closed during patient expiration. This arrangement is particularly useful for patients that suffer from pulmonary edema, which may cause fluid to build up in the lungs that may be expired through the IRV 100. Due to the one-way valve arrangement of IRV 100, any fluids (expiratory gases and/or pulmonary edema fluid) is directed through the one-way valve 114 and out the expiratory port 116, thereby preventing any pulmonary edema fluid from passing through and/or obstructing the proper operation of one-way valves 108 and 112. In some embodiments, a collection bag or other container may be coupled with the expiratory port 116 and/or lumens 102 to collect any fluids emitted from the IRV 100. Additionally, the valve arrangement of IRV 100 effectively separates the inspiratory flow from the expiratory flow such that expiratory carbon dioxide-rich gases will not be mixed with inspiratory gases. This enables the delivery of higher concentrations of oxygen to the patient during CPR, thereby allowing higher oxygenation levels within the patient's bloodstream and resulting in improved resuscitation outcomes.

Figure 1E:
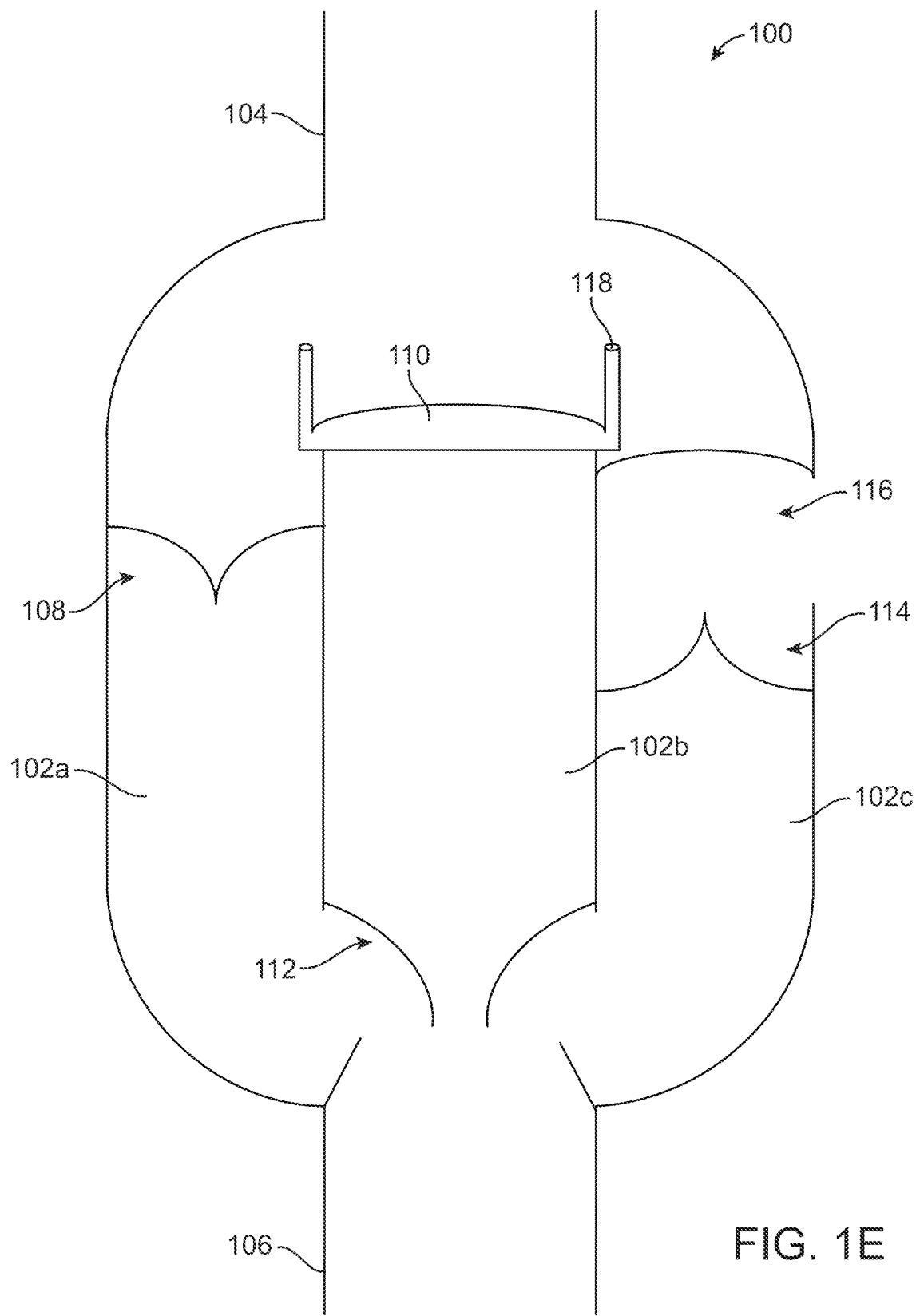
FIG. 1E illustrates a state of the IRV of FIG. 1A during a decompression phase of CPR.

During the decompression phase of CPR, the chest wall recoils as the rescuer's hands (or chest compression device) are lifted. In the case of ACD-CPR, the chest is actively decompressed, such as by using a suction cup and/or adhesive to draw the chest upward. During this phase of CPR, a negative pressure is created within the chest (below the cracking pressure of the one-way valve 108). FIG. 1E illustrates the state of IRV 100 during the decompression phase of CPR. Here, the one-way valves 108 and 114, as well as diaphragm 110, are closed, thereby preventing respiratory gases from entering the patient. By preventing respiratory gases from entering the patient over multiple cycles of chest compressions and chest recoil, less and less air is present within the thorax, providing room for more and more blood to return to the heart during the chest wall recoil phase. This increases circulation to the coronary arteries and lowers intracranial pressure during the chest wall decompression phase, resulting in greater rates of successful resuscitation outcomes. In addition, during the decompression phase of CPR the pressures within the chest remain sub-atmospheric at a level determined by the upward chest wall recoil (which may be passive or active) when the anterior chest wall is actively pulled upward when the patient is in the supine position.

Figure 2A:
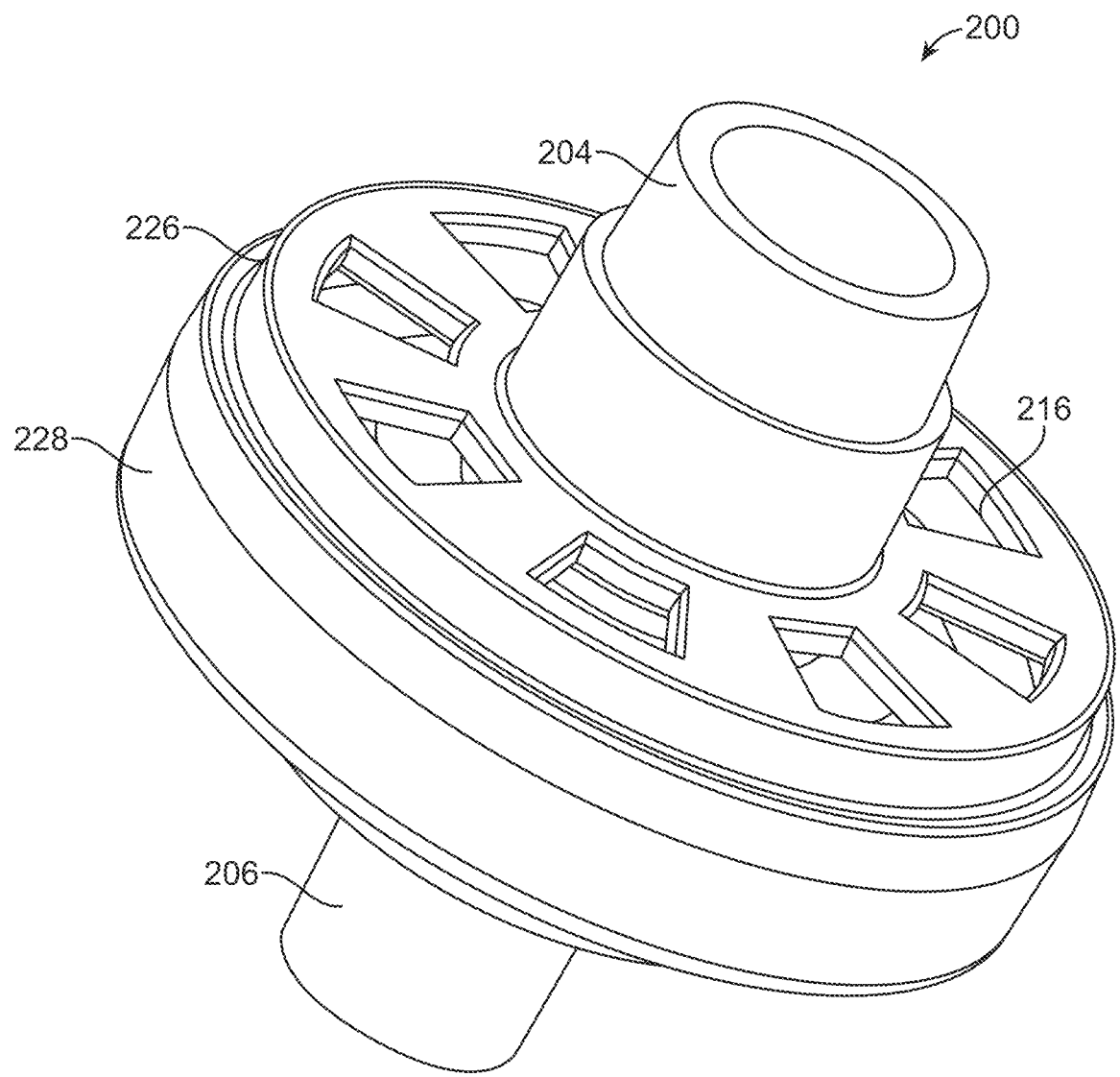
FIG. 2A illustrates a perspective view of an IRV according to embodiments.

An embodiment of an IRV 200 is illustrated in FIG. 2A. IRV 200 may function in a similar manner as IRV 100 and may include any of the features described above. IRV 200 includes a housing 220 that includes a top cap 226 having a ventilation port 204 for actively providing respiratory gases to the patient and a bottom cap 228 having a patient port 206 that is configured to mate with a patient interface such as a facial mask, an endotracheal tube, supraglottic airway device, other airway device and/or other interface (not shown). The housing 220 defines an interior in which a valve structure similar to the arrangement of valves in IRV 100 is disposed. In some embodiments, the housing 220 defines a number of inspiration/expiration ports 216 that allow expiratory gases and/or other fluids to be ejected from the IRV 200 and/or inspiratory gases to enter the IRV 200 in the event of spontaneous inspiration. In some embodiments, the inspiration/expiration ports 216 may be separate, such that each individual port 216 is usable only for inspiration or expiration. As illustrated, the inspiration/expiration ports 216 are disposed in a radial pattern through a surface of the top cap 226, however other arrangements and/or numbers of inspiration/expiration ports 216 are possible.

Figure 2B:
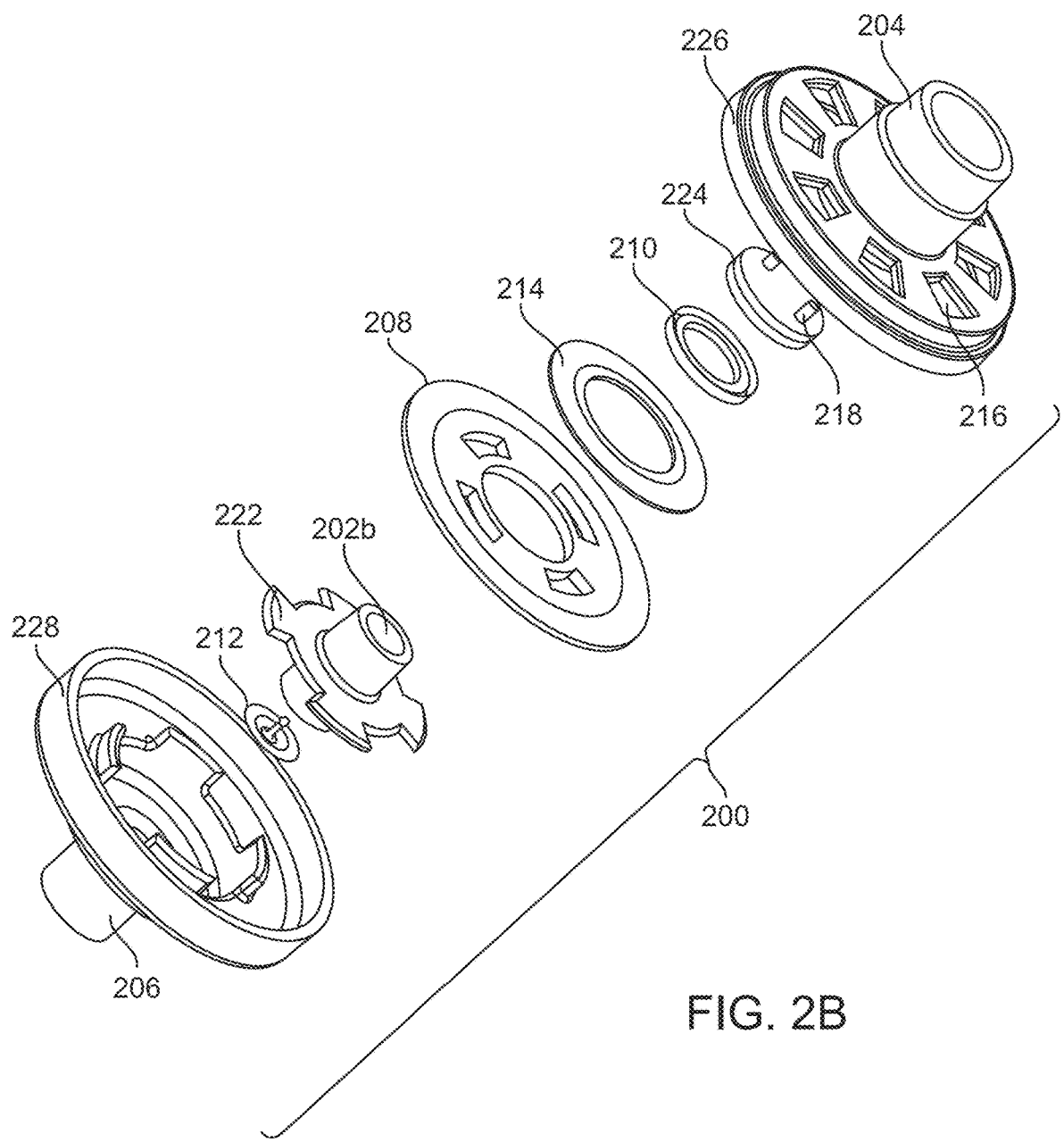
FIG. 2B illustrates an exploded view of the IRV of FIG. 2A.
Figure 2C:
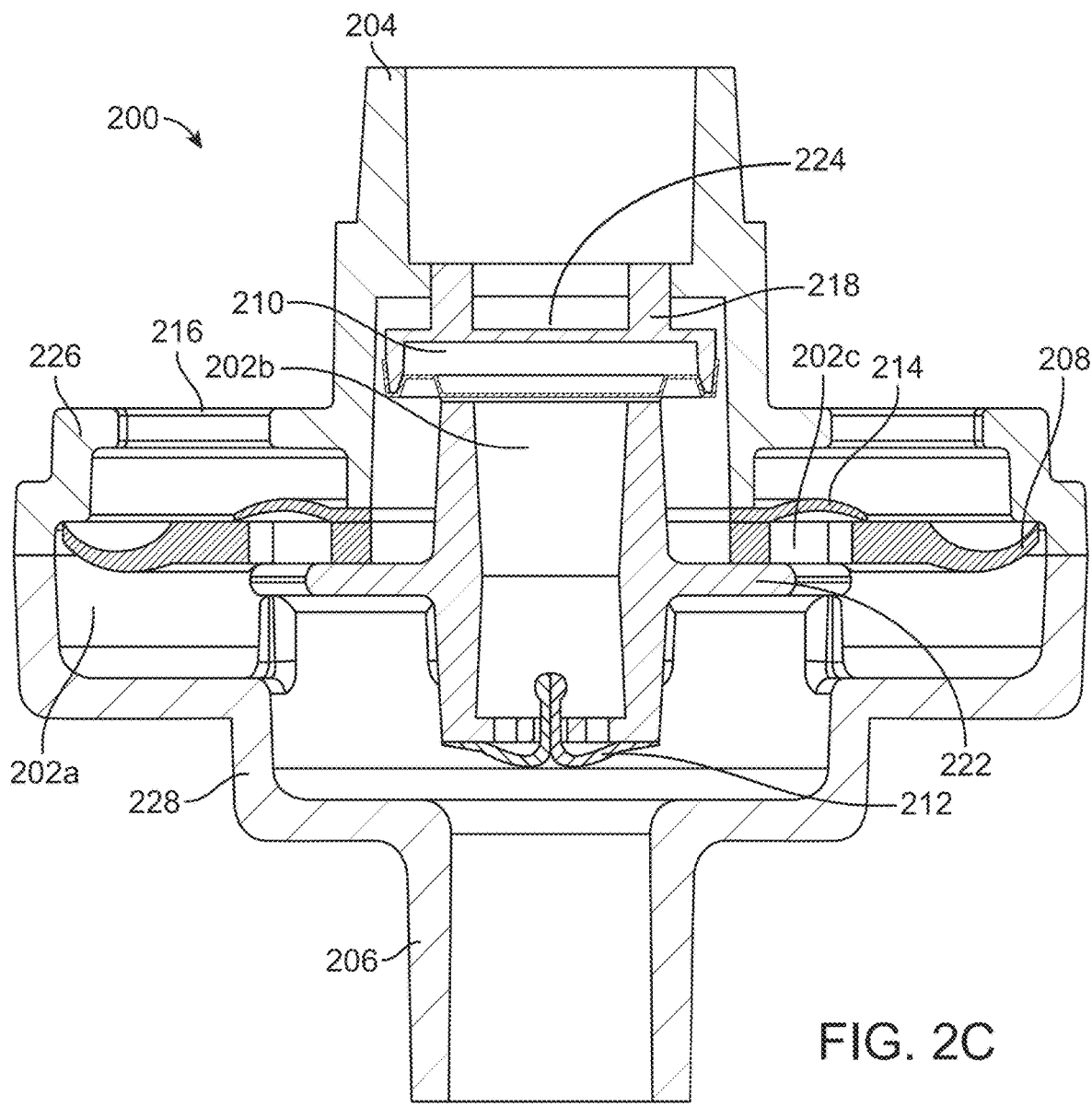
FIG. 2C illustrates a front cross-sectional view of the IRV of FIG. 2A.

FIGS. 2B and 2C illustrate the interior components of the IRV 200. In contrast to the parallel arrangement of lumens 102 in IRV 100, IRV 200 includes three concentric fluid paths, although other arrangements are possible. As illustrated, a central support 222 provides a central lumen 202b that serves as a positive pressure flow path, similar to positive pressure lumen 102b. A diaphragm 210 is positioned against a top surface of the central lumen 202b to seals a top end of the central lumen 202b, while a floating backflow valve 212 is positioned within and/or at a bottom end of the central lumen 202b that permits air to pass into the patient port 206 and subsequently delivered to the patient's airways while preventing expiratory fluids from entering the central lumen 202b and/or the ventilation port 204. The floating backflow valve 212 may be similar to one-way valve 112 described above.

While illustrated as a fish mouth valve, it will be appreciated that floating backflow valve 212 may be any form of one-way valve, such as a check valve, duck bill valve, spring valve, non-rebreather valve, etc. In some embodiments, the diaphragm 210 may have a cracking pressure that is substantially equal to atmospheric pressure such that positive pressure respirations may move and/or deform the diaphragm 210 such that the positive pressure air may be delivered to an interior of the central lumen 202b. In some embodiments, to provide a diaphragm 210 that has a cracking pressure that is substantially equal to atmospheric pressure, the diaphragm 210 and/or a diaphragm holder 224 may include one or more ventilation ports 218 that enable airflow attributed to the movement of the diaphragm 210 to pass through to minimize any air resistance associated with the moving diaphragm 210. Once past the diaphragm 210, the incoming positive pressure airflow then forces the floating backflow valve 212 open and passes into the patient's airways via the patient port 206. The one-way valve 212 may have a cracking pressure that is less than 1 mmHg, and possible 0 mmHg such that any positive pressure respiration may cause the one-way valve 212 to open. By designing the diaphragm 210 and the one-way valve 212 to have low cracking pressures, the respiratory gases pass through the IRV 200 and into the patient's airways with minimal or no resistance from the IRV 200. In some embodiments one-way valve 212 opens with each positive pressure breath and simultaneously blocks respiratory gases from exiting through the expiratory port 216. In such configurations one-way valve 212 may preferably be designed as a fish-mouth or duck bill valve serving three functions: 1) to prevent backflow of gases and fluids from the lungs and thus prevent such fluids from disabling diaphragm 210 and the pressure response valve 208, 2) to prevent mixture of inhaled and exhaled gases, thus preventing a reduction in oxygen delivered to the patient, and 3) to occlude the expiratory port structure during a positive pressure breath. In addition, this approach allows for the measure of minute volumes during ventilation if flow sensors are used in the IRV.

IRV 200 also defines an expiratory flow path 202c, which operates in a similar manner as expiratory lumen 102c described above. As illustrated, the expiratory flow path 202c is generally annular in shape and extends about the central lumen 202b. The expiratory flow path 202c is configured to enable expiratory gases and/or other fluids from the patient to be evacuated out of the IRV 200. The expiratory flow path 202c includes an exhalation valve 214 that may be similar to one-way valve 114. Exhalation valve 214 leads to the inspiration/expiration ports 216. The expiratory flow path 202c may be sealed from the ventilation port 204 and central lumen 202b so as to prevent any expiratory fluids from passing through the ventilation port 204 and central lumen 202b. For example, the floating backflow valve 212 and solid walls of the housing 220 prevent the expiratory flow path 202c from being in fluid communication with the ventilation port 204 and central lumen 202b during operation of the IRV 200. The exhalation valve 214 has a cracking pressure of between about 0 and 10 mmHg or may be variable and adjustable. This enables the exhalation valve 214 to open when fluids (gas and/or liquids) are expelled from the patient's airways, thereby allowing the fluids to exit the IRV 200 via the inspiration/expiration ports 216. For example, delivery of chest compressions during CPR forces air out of the patient's lungs. This air may pass through the exhalation valve 214 and out the inspiration/expiration ports 216. Similarly, patient expiration may flow through the exhalation valve 214 and out the inspiration/expiration ports 216. In some embodiments, pulmonary edema may occur, causing fluids that may get expired by the patient and delivered into the IRV 200 via the patient port 206. These fluids may also pass through the exhalation valve 214 and out the expiratory port.

IRV 200 also defines patient inspiratory flow path 202a, which operates in a similar manner as patient inspiration lumen 102a described above. As illustrated, the patient inspiratory flow path 202a is generally annular in shape and extends about the central lumen 202b. The patient inspiratory flow path 202a partially overlaps with a lower portion of the expiratory flow path 202c and extends annularly outward of an upper portion of the expiratory flow path 202c where it connects with the inspiration/expiration ports 216. As illustrated, the patient inspiratory flow path 202a includes a vacuum valve 208 that operates in a similar manner as one-way valve 108 described above. For example, the vacuum valve 208 operates as a safety valve to enable respiratory gases to be drawn into the patient's airway via the ventilation port 204 in the event of spontaneous inspiration by the patient. Oftentimes, the vacuum valve 208 has a cracking pressure of between about −5 and −20 mm Hg.

While the expiration valve 214 and vacuum valve 208 are illustrated as being generally annular in shape, it will be appreciated that other forms of valves are possible in some embodiments. For example, one of both of the valves may be in the form of discrete valves at one or more locations in the IRV 200. As just one example, the expiration valve 214 and vacuum valve 208 may be in the form of fish mouth valves or duck-bill valves. The IRV 200 may include one or more of each valve positioned at discrete locations.

Figure 2D:
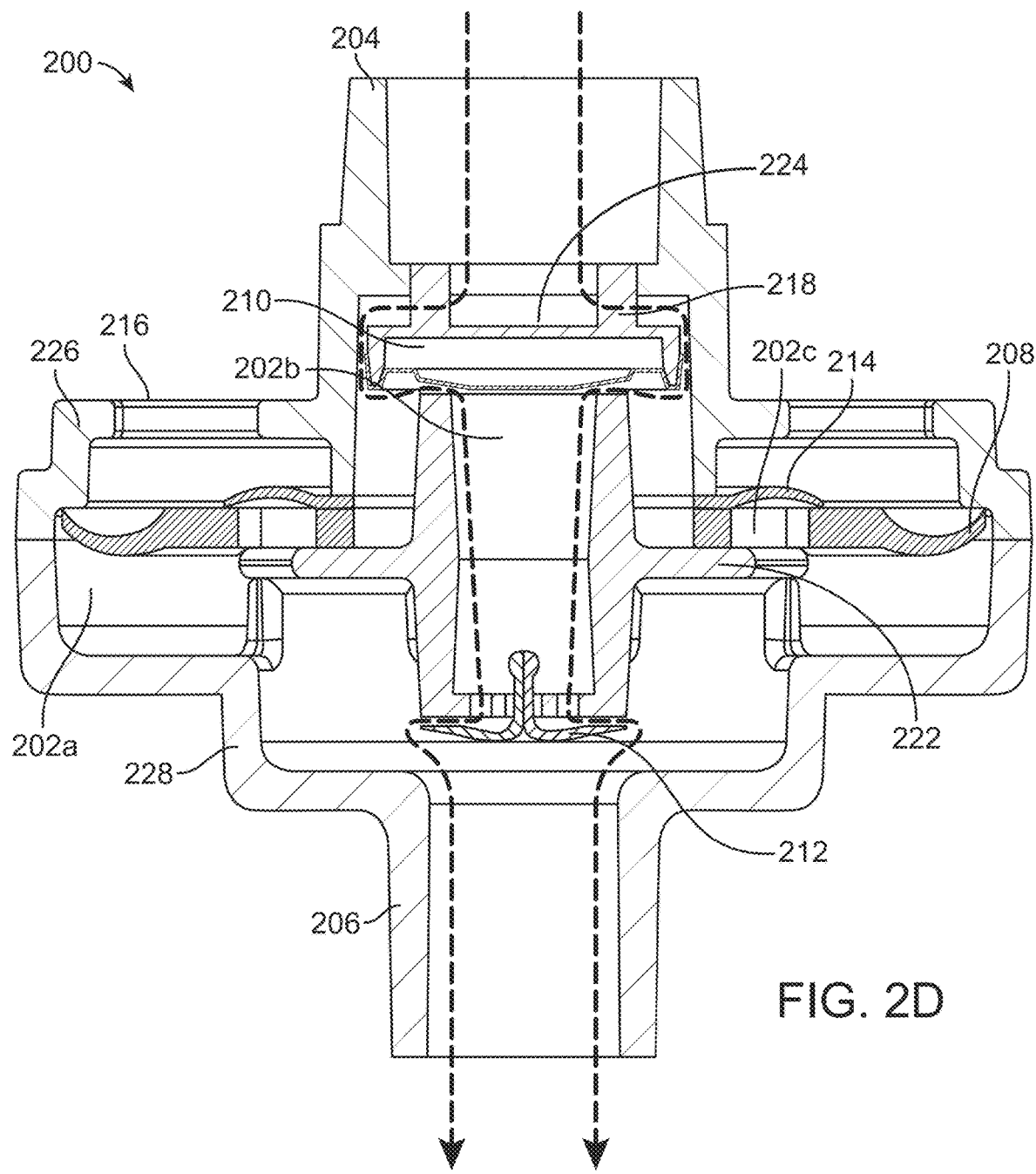
FIG. 2D illustrates airflow through the IRV of FIG. 2A during delivery of a positive pressure ventilation.

FIGS. 2D-2G illustrate the operation of the IRV 200 under different respiration conditions. The arrows in FIG. 2D illustrate airflow through the IRV 200 during delivery of a positive pressure ventilation. Positive pressure ventilations may be delivered using a manual and/or automated respirator that is coupled with the ventilation port 204. For example, ventilations may be delivered using mouth-to-mouth ventilation, a mouth-mask, a resuscitator bag, an automatic or semi-automatic ventilator, a body cuirass or iron lung like device and/or the like. During ventilation, air is typically forced into the IRV 200 via the ventilation port 204 and flows around the diaphragm 210 until it contacts an underside of the diaphragm 210. This airflow causes the diaphragm 210 to move and/or deform to allow the airflow to enter the central lumen 202b. The air then forces open the floating backflow valve 212 and is delivered to the patient's airway via the patient port 206. Backflow valve 212, which is preferably a duck bill or fish mouth valve, also closes off the expiratory flow path 202c in the process, assuring that the positive pressure breath is delivered to the patient. During positive pressure ventilations, the vacuum valve 208 and exhalation valve 214 remain closed, such that all air delivered by the respirator is delivered to the patient.

Figure 2E:
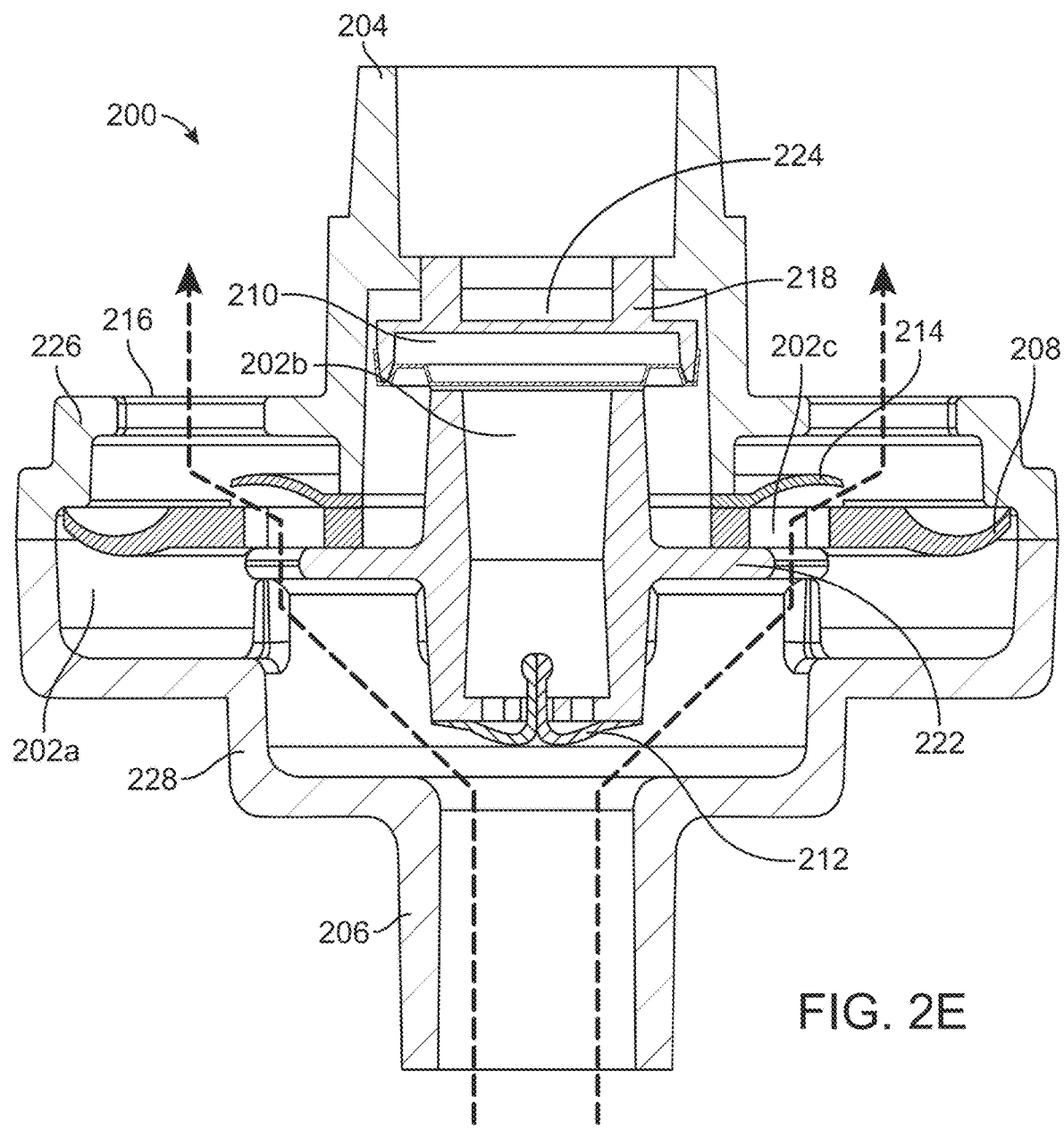
FIG. 2E illustrates airflow through the IRV of FIG. 2A during spontaneous inspiration.

In some cases, the patient may spontaneously inspire, creating a negative pressure within the chest that causes air to be drawn into the inspiration/expiration ports 216 as demonstrated by the arrows in FIG. 2E. As the air is being drawn in through the inspiration/expiration ports 216, rather than pushed in through the ventilation port 206, the diaphragm 210 remains positioned against the top surface of the central lumen 202b and the floating backflow valve 212 remains closed, thereby sealing the central lumen 202b and preventing air from passing through. When the force of the patient's inspiration exceeds the cracking pressure of the vacuum valve 208, the vacuum valve 208 opens and respiratory gases are drawn into the patient's airways via the patient inspiratory flow path 202a and patient port 206 as illustrated here. The vacuum valve 208 may be a spring-load valve, a mushroom valve, a strain-gauge valve, and/or other type of pressure sensitive valve. The vacuum valve 208 may have a preset cracking or opening pressure of between approximately −5 to −20 cm H2O. During spontaneous inspiration, the negative pressure within the chest maintains the exhalation valve 214 in a closed position.

Figure 2F:
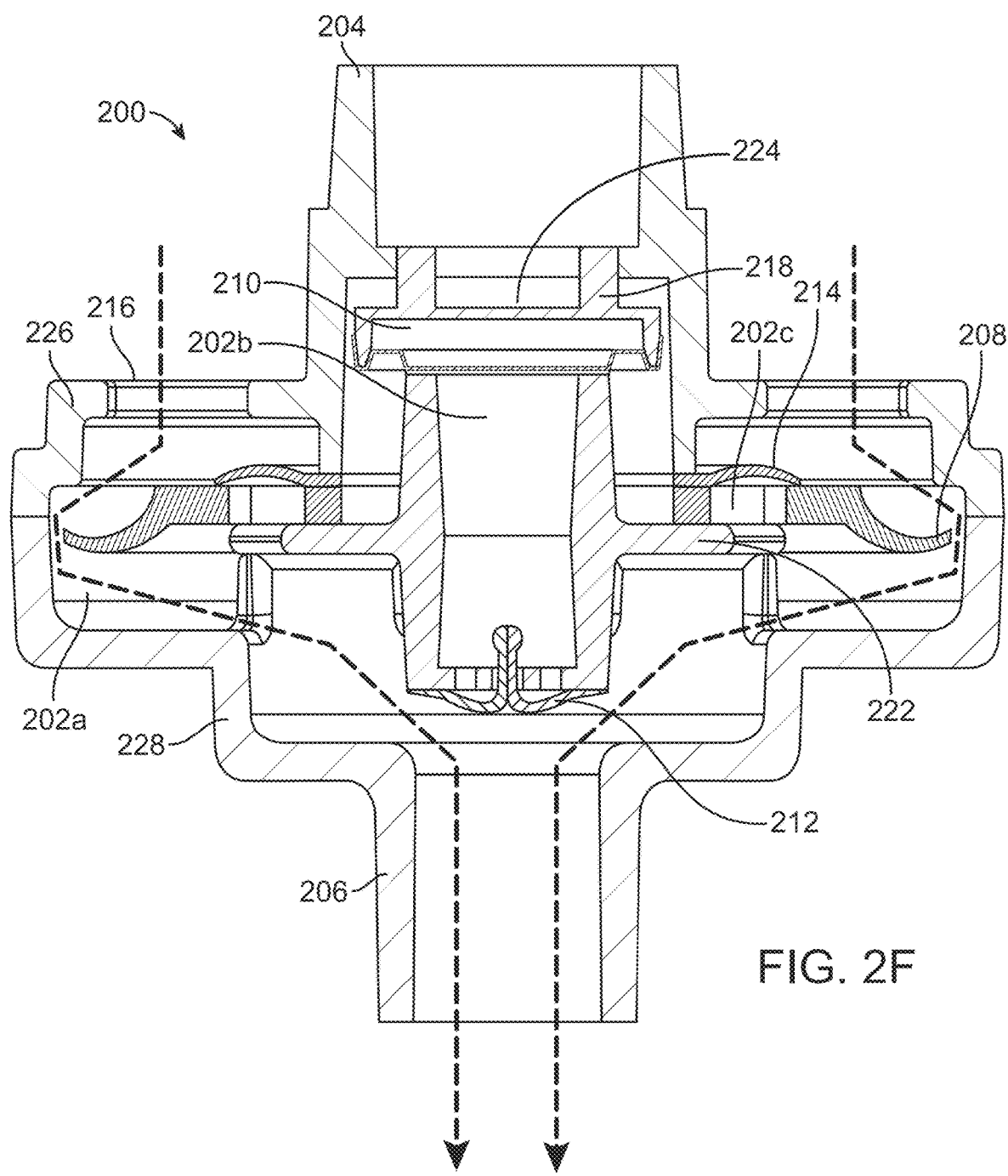
FIG. 2F illustrates airflow through the IRV of FIG. 2A during a chest compression phase of CPR or a patient expiration.

When the chest is compressed (manually and/or automatically) and/or the patient expires, respiratory gases flow from the patient and out through the IRV 200 as shown by the arrows in FIG. 2F. For example, expiratory gases pass through the patient port 206 and force the exhalation valve 214 to open. The expiratory gases then flow through the exhalation valve 214 and out the inspiration/expiration ports 216. Due to the direction of operation of the vacuum valves 208 and floating backflow valve 212, these valves 208, 212 are both closed during patient expiration. This arrangement is particularly useful for patients that suffer from pulmonary edema, which may cause fluid to build up in the lungs that may be expired through the IRV 200. Due to the one-way valve arrangement of IRV 200, any fluids (expiratory gases and/or pulmonary edema fluid) is directed through the exhalation valve 214 and out the inspiration/expiration ports 216, thereby preventing any pulmonary edema fluid from passing through and/or obstructing the proper operation of vacuum valve 208 and floating backflow valve 212. Additionally, the valve arrangement of IRV 200 effectively separates the inspiratory flow from the expiratory flow such that expiratory gases will not be mixed with inspiratory gases. This enables the delivery of higher concentrations of oxygen to the patient during CPR, thereby allowing higher oxygenation levels within the patient's bloodstream and resulting in improved resuscitation outcomes.

Figure 2G:
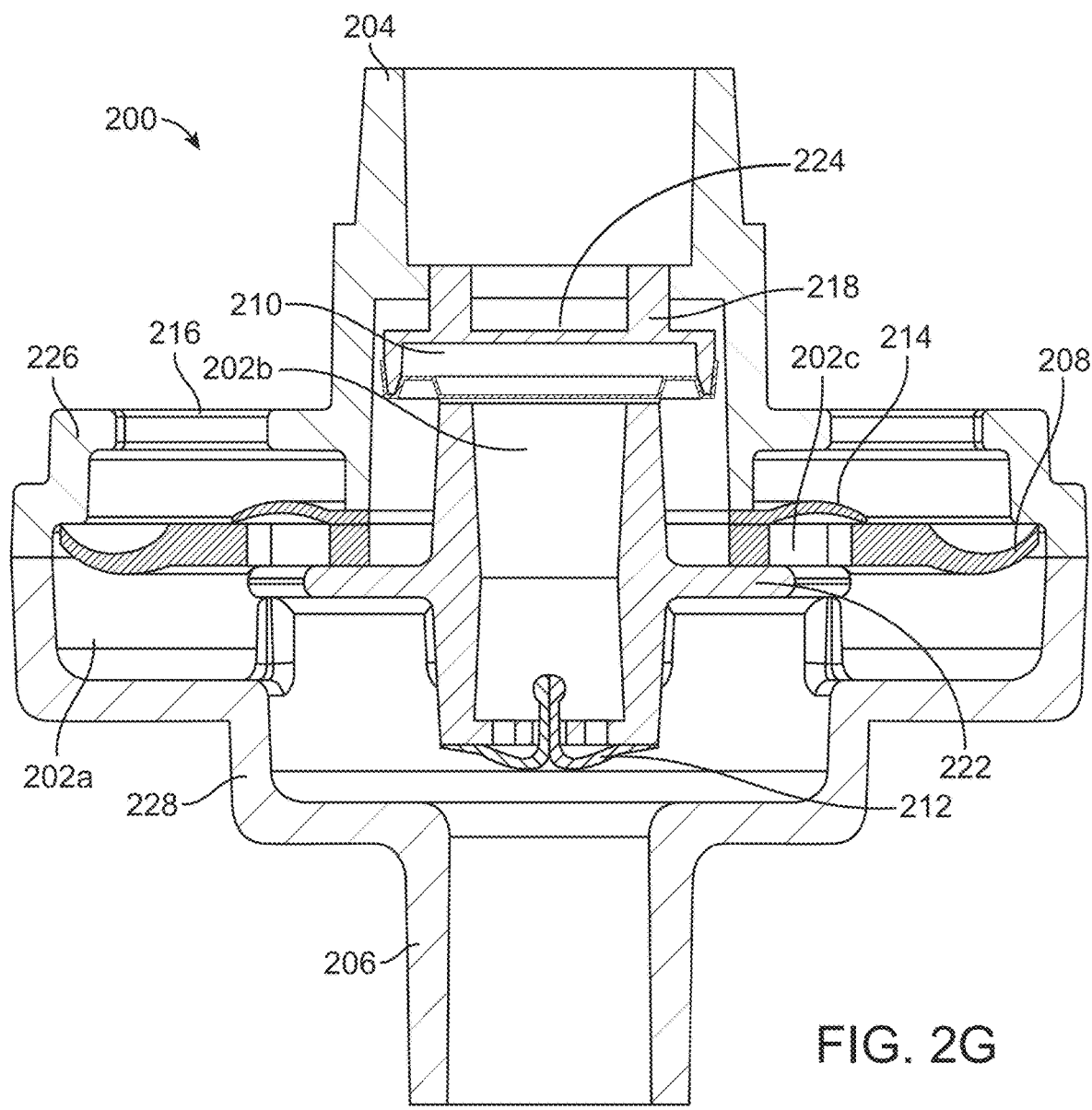
FIG. 2G illustrates a state of the IRV of FIG. 2A during a decompression phase of CPR.

During the decompression phase of CPR, the chest wall recoils as the rescuers hands are lifted. In the case of ACD-CPR, the chest is actively decompressed, such as by using a suction cup and/or adhesive to draw the chest upward. During this phase of CPR, a negative pressure is created within the chest (below the cracking pressure of the vacuum valve 208). FIG. 2G illustrates the state of IRV 200 during the decompression phase of CPR. Here, the vacuum valve 208, exhalation valve 214, and diaphragm 210, are closed, thereby preventing respiratory gases from entering the patient. By preventing respiratory gases from entering the patient over multiple cycles of chest compressions and chest recoil, less and less air is present within the thorax, providing room for more and more blood to return to the heart during the chest wall recoil phase. Moreover, the pressure within the chest becomes more negative. This pulls more venous blood black into the thorax, increases circulation to the coronary arteries, and lowers intracranial pressure during the chest wall decompression phase, resulting in greater rates of successful resuscitation.

It is important to note that the drawings shown herein represent the potential path for gas exchange into and out of the patient but the dimensions in IRV 200 are representative but not exactly to scale and only one of a multitude of potential valve mechanisms (e.g. duck bill, ball valve, annular valve, circular valve, a butterfly valve, a check valve, balloon valve, fish mouth, mushroom, disk valve, etc.) in shown in FIGS. 2A-2G.

In addition to the IRV as shown, it is important to note that additional features may be incorporated within the IRV system that could include a battery-operated timing light to help guide ventilations at a given rate, sensors that measure pressures within the IRV, electronic components that provide physiological sensing and receive and/or transmit signals to a separate receiver, and/or a microphone and electronic system that can provide auditory signals and instructions (e.g. tell the rescuer to ventilate faster or slower).

Figure 3A:
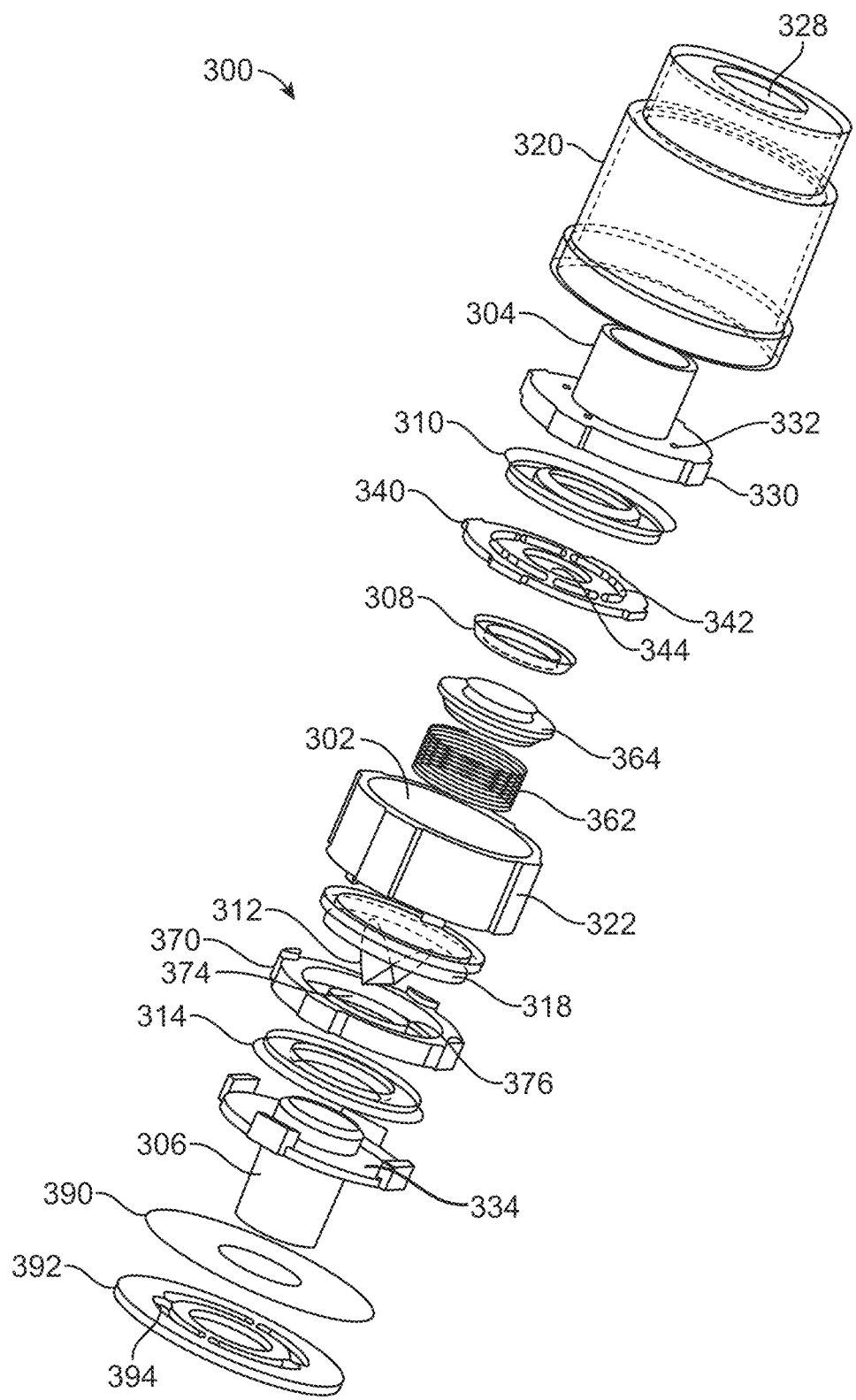
FIG. 3A illustrates an exploded view of an IRV according to embodiments of the present invention.
Figure 3B:
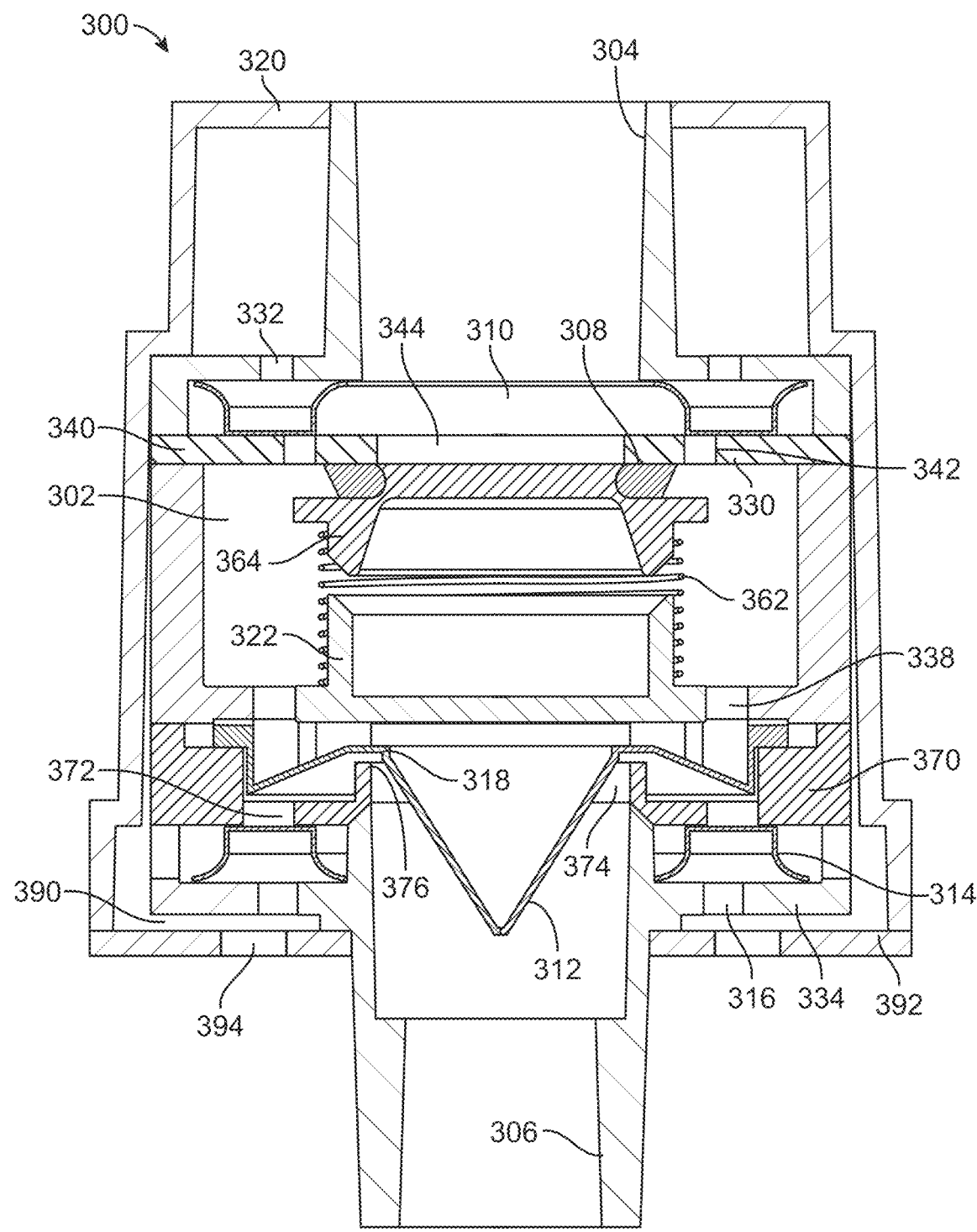
FIG. 3B illustrates a front cross-sectional view of the IRV of FIG. 3A.

An embodiment of an IRV 300 is illustrated in FIGS. 3A and 3B. IRV 300 may function in a similar manner as IRVs 100 and 200 and may include any of the features described above. IRV 300 includes a housing 320 that defines a central aperture 328 that may receive a ventilation port 304 for coupling the IRV 300 to a ventilation device. The ventilation port 304 may include a flange 330 that may fit within an interior of the housing 320 and maintain the ventilation port 304 in place within the central aperture 328. The flange 330 may define a number of apertures 332 that extend through a thickness of the flange 330 at positions that are radially outward of the central aperture 328. Apertures 332 may be in fluid communication with an atmospheric pressure source. IRV 300 may include a patient port 306 that is configured to mate with a patient interface such as a facial mask, an endotracheal tube, other airway device and/or other interface (not shown). Patient port 306 may have a similar structure as ventilation port 304, and may include a flange 334 that defines a number of expiratory ports 316 that are in the form of apertures. The housing 320 defines an interior in which a valve structure similar to the arrangement of valves in IRVs 100 and 200 is disposed. Expiration ports 316 may expose a backside of one or more valves of IRV 300 to atmospheric pressure.

Similar to IRV 200, IRV 300 may include three concentric fluid paths, although other arrangements are possible. As illustrated, a central support 322 defines a central lumen 302, which may be annular in shape. Annular lumen 302 may serve as a positive pressure flow path, similar to positive pressure lumen 102b and/or 202b. A bottom of the central support 322 may define a number of apertures 338 that are fluidly coupled with the annular lumen 302. A diaphragm 310 may seal a top end of the annular lumen 302. Diaphragm 310 may have a cracking pressure that is substantially equal to atmospheric pressure. A one-way valve 312, such as a duck-bill valve, is positioned within and/or at a bottom end of the annular lumen 302 that permits air to pass into the patient port 306 and subsequently delivered to the patient's airways while preventing expiratory fluids from entering the annular lumen 302 and/or the ventilation port 304. The one-way valve 312 may be similar to one-way valve 112 and/or floating backflow valve 212 described above. In operation, positive pressure airflow may open and flow through the diaphragm 310 and then force the one-way valve 312 open before passing into the patient's airways via the patient port 306. The one-way valve 312 may have a cracking pressure that is less than 1 mmHg, and possibly 0 mmHg such that any positive pressure respiration may cause the one-way valve 312 to open. By designing the diaphragm 310 and the one-way valve 312 to have low cracking pressures, the respiratory gases pass through the IRV 300 and into the patient's airways with minimal or no resistance from the IRV 300.

A center plate 340 may be seated atop the central support 322 beneath the flange 330 of the ventilation port 304. The center plate 340 may define a number of apertures 342 arranged in an annular pattern. The center plate 340 may also define a central aperture 344, which may serve as an inspiratory port that enables inspiratory gases to enter the IRV 300 in the event of spontaneous inspiration. The apertures 342 of the center plate 340 may be aligned with the apertures 332 of the flange 330. Atmospheric diaphragm 310 may be positioned between the apertures 342 and the apertures 332. The atmospheric diaphragm 310 may enable airflow to enter the IRV 300 via the apertures 332 and apertures 342 when a particular cracking pressure is met, as will be described in greater detail below.

A safety check valve assembly may be disposed within the central support 322 to allow for spontaneous breathing through a low level of resistance. For example, a safety check valve 308 may be positioned about the central aperture 344 of the center plate 340. The safety check valve 308 may be configured to seal the central aperture 344 of the center plate 340 when in a closed position and may allow airflow to enter the annular lumen 302 when in an open position. The safety check valve 308 may be biased toward the closed position by a spring 362. For example, a base of the spring 362 may be positioned against a base of the central support 322 and a top of the spring 362 may press against a piston 364. Piston 364 may be disposed against an underside of the safety check valve 308. The spring force of the spring 362 may be selected to provide a cracking pressure of the safety check valve 308 in a range of −5 to −20 cm of water, and oftentimes less than about −12 cm of water. This may enable the safety check valve 308 to open and deliver air to the patient port 306 if a strong enough vacuum is created as the chest recoils if a patient is receiving CPR and/or if a patient takes a spontaneous breath.

An expiratory port plate 370 may be interfaced with a bottom end the central support 322. The expiratory port plate 370 may define a number of apertures 372 that are in fluid communication with the annular lumen 302. The apertures 372 may be in alignment with the expiratory ports 316 of the flange 334 of the patient port 306. The expiratory port plate 370 may also define a central aperture 374 that is aligned with the patient port 306 and may receive an end of the one-way valve 312. A valve seat 376 may be disposed about the central aperture 374. Valve seat 376 enables an outer surface 318 of one-way valve 312 to seal off an expiratory flow path of the IRV 300 when the outer surface 318 is pressed against the valve seat 376. An exhalation valve 314 may be disposed between the apertures 372 and expiratory ports 316. Expiratory ports 316 may provide atmospheric pressure to a backside of the exhalation valve 314 to maintain the exhalation valve 314 in a closed position in the absence of pressure from expiratory fluids. Exhalation valve 314 may be annular in shape, and may be a one-way valve that is oriented such that the exhalation valve 314 prevents airflow from entering the IRV 300 through apertures 372, while enabling expiratory flow to exit the IRV via apertures 372.

In some embodiments, a filter 390 may be provided below the apertures 372. The filter 390 may be a HEPA filter that may prevent harmful germ particles (bacterial and viral) from contaminating the air around the patient, thus protecting rescuers from possible infection. A filter plate 392 may be positioned below the filter 390 and may couple with a bottom end of the housing 320 to secure the internal components of IRV 300 within the housing 320. The filter plate 392 may define a number of outer exhalation ports 394 that enable expiratory air to be filtered and subsequently vented or otherwise expelled and from the interior of the IRV 300.

In some embodiments, the one-way valve 312 and outer surface 118 of one-way valve 312 may be operate as a single 'non-rebreather' valve proximate the patient port 306, which may prevent the mixture of inspiratory and expiratory flow. For example, opening of a central valve portion (e.g., a duck bill valve, etc.) of the one-way valve 312 may enable positive pressure ventilation from the ventilation port 304 to patient port 306 to be substantially resistant free, while the outer surface 118 is positioned against valve seat 376 to seal off the expiratory flow path. When respiratory gases leave the patient, either when the chest is compressed or the patient blows out, these gases shunt out the non-rebreather valve by pressing outer surface 118 away from the valve seat 376 to open up the expiratory flow path to expel the respiratory air from the IRV 300 via outer exhalation ports 304 and/or through the filter 390, while the central valve portion of the one-way valve 312 is closed to seal off the inspiratory flow path. The use of such a non-rebreather valve may provide several benefits. For example, such a valve may eliminate or reduce the possibility of rebreathing expired carbon dioxide-rich gas provided the dead space of the valve is small, enables the IRV 300 to be utilized in spontaneous and/or controlled respiration applications, and may enable minute air flow volumes to be measured.

IRV 300 defines an expiratory flow path, which operates in a similar manner as expiratory lumen 102c and expiratory flow path 202c described above. The expiratory flow path is generally annular in shape and extends about the central lumen 302. The expiratory flow path enables expiratory gases and/or other fluids from the patient to be evacuated out of the IRV 300. The expiratory flow path extends from the patient port 306, through a gap between the valve seat 376 and the outer surface 318 of the one-way valve 312 and passes through the apertures 372, exhalation valve 314, and filter 390 before exiting through outer exhalation ports 394. For example, the pressure from the expiratory flow may force the entire one-way valve 312 upward such that the outer surface 318 disengages from the valve seat 376 to form a gap that provides access to the expiratory flow path. The expiratory flow path may be sealed from the ventilation port 304 and annular lumen 302 so as to prevent any expiratory fluids from passing through the ventilation port 304 and annular lumen 302. For example, the one-way valve 312 and solid walls of the housing 320 prevent the expiratory flow path from being in fluid communication with the ventilation port 304 and annular lumen 302 during operation of the IRV 300. The exhalation valve 314 has a cracking pressure of between about 0 and 10 mmHg or may be variable and adjustable. This enables the exhalation valve 314 to open when fluids (gas and/or liquids) are expelled from the patient's airways, thereby allowing the fluids to exit the IRV 300 via the outer exhalation ports 394. For example, delivery of chest compressions during CPR forces air out of the patient's lungs. This air may pass through the exhalation valve 314 and out the outer exhalation ports 394. Similarly, patient expiration may flow through the exhalation valve 314 and out the outer exhalation ports 394. In some embodiments, pulmonary edema may occur, causing fluids that may get expired by the patient and delivered into the IRV 300 via the patient port 306. These fluids may also pass through the exhalation valve 314 and out the outer exhalation ports 394.

IRV 300 also defines patient inspiratory flow path, which operates in a similar manner as patient inspiration lumen 102a and patient inspiratory flow path 202a described above. The patient inspiratory flow path is generally annular in shape and extends about the annular lumen 302. The patient inspiratory flow path partially overlaps with a lower portion of the expiratory flow path and extends annularly outward of an upper portion of the expiratory flow path where it connects with the safety check valve 308. For example, the patient inspiratory flow path may extend from ventilation port 304 and through central aperture 344 of the center plate 340, safety check valve 308, annular lumen 302, apertures 338, one-way valve 312, and the patient port 306. The safety check valve 308 may open to enable respiratory gases to be drawn into the patient's airway via the central aperture 344 in the event of spontaneous inspiration by the patient. Oftentimes, the safety check valve 308 has a cracking pressure of between about −5 and −20 mm Hg.

While the expiration valve 314 and safety check valve 308 are illustrated as being generally annular in shape, it will be appreciated that other forms of valves are possible in some embodiments. For example, one of both of the valves may be in the form of discrete valves at one or more locations in the IRV 300. As just one example, the expiration valve 314 and safety check valve 308 may be in the form of fish mouth valves or duck-bill valves. The IRV 300 may include one or more of each valve positioned at discrete locations.

Figure 3C:
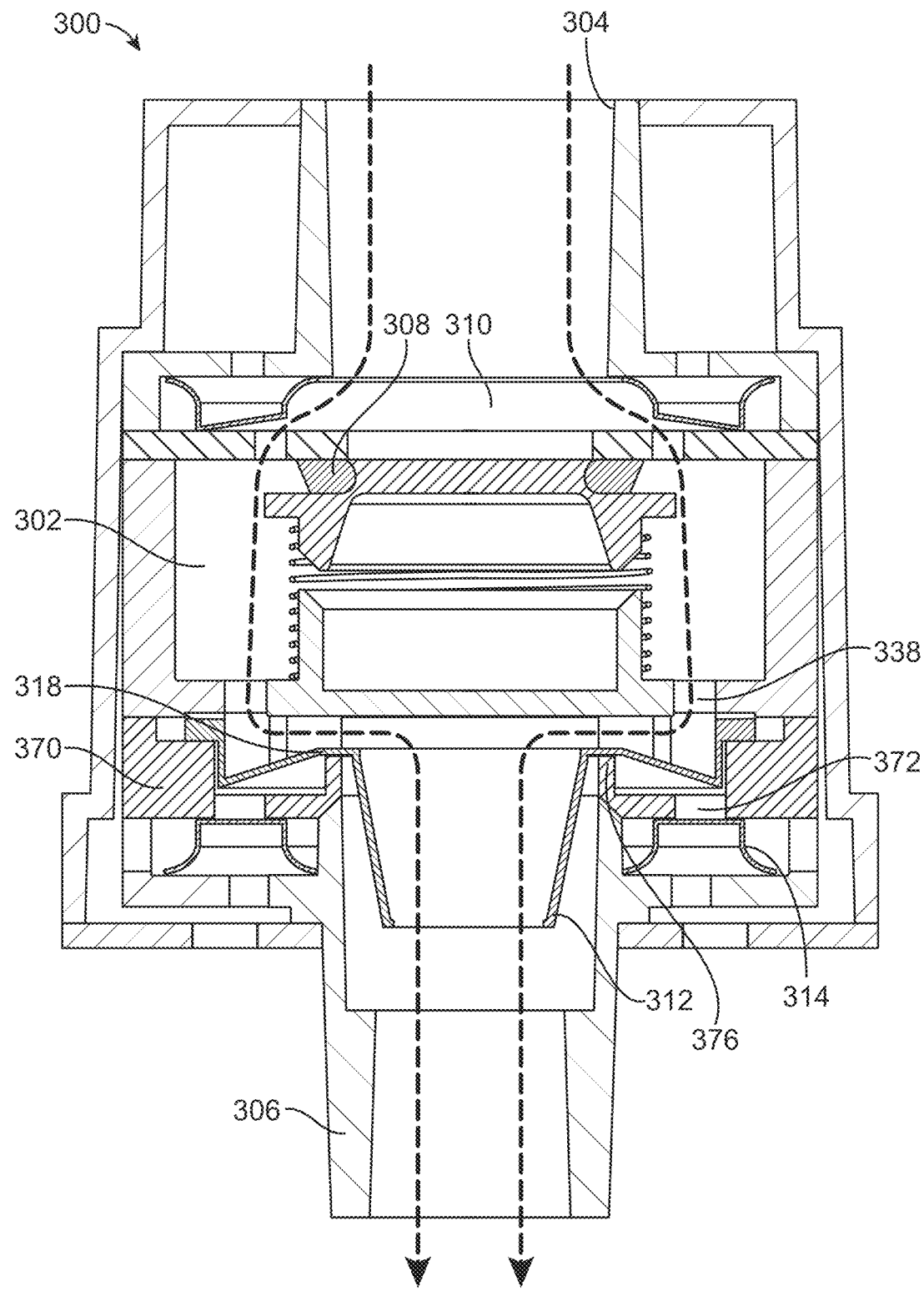
FIG. 3C illustrates airflow through the IRV of FIG. 3A during delivery of a positive pressure ventilation.
Figure 3D:
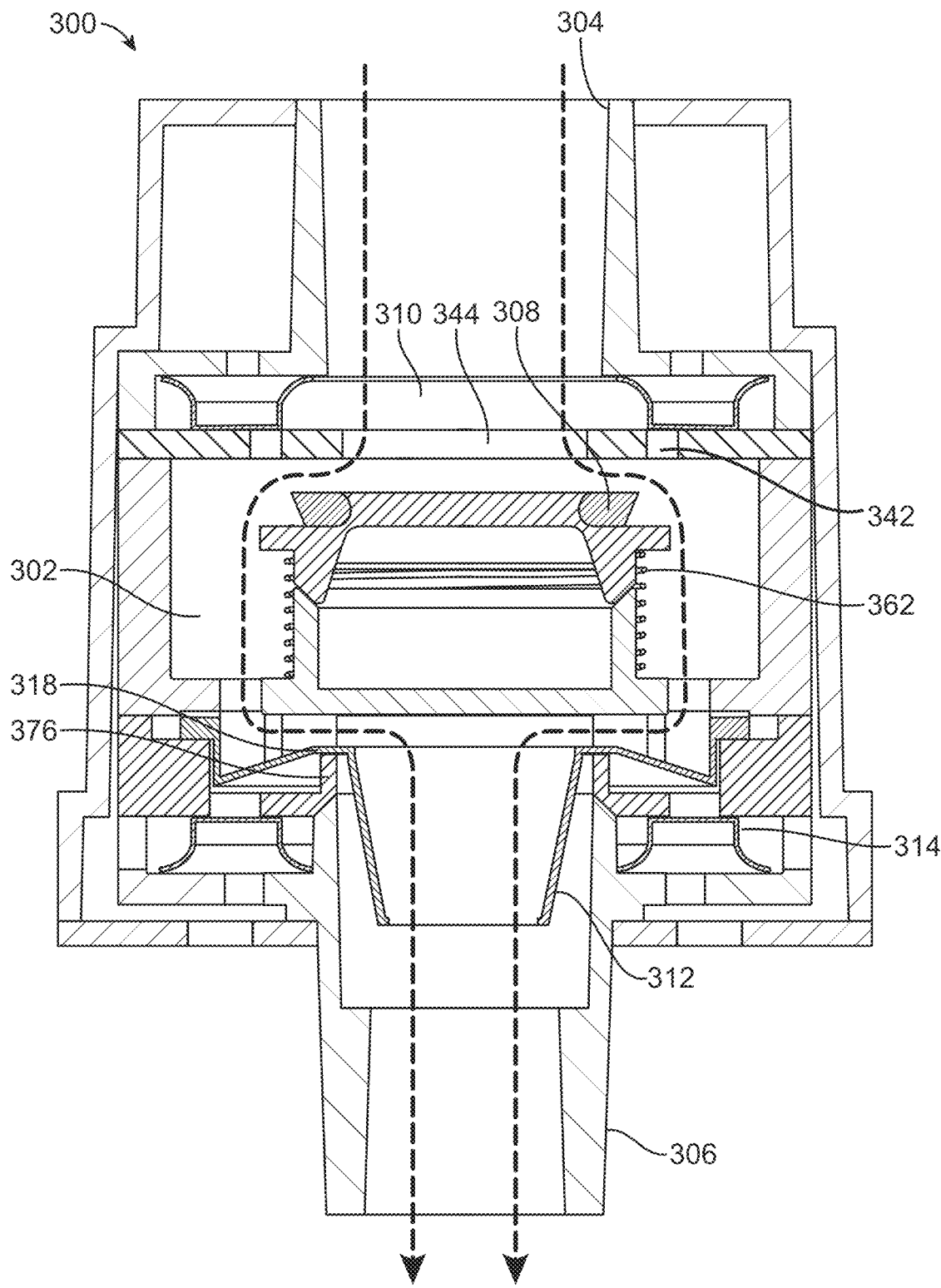
FIG. 3D illustrates airflow through the IRV of FIG. 3A during spontaneous inspiration.
Figure 3E:
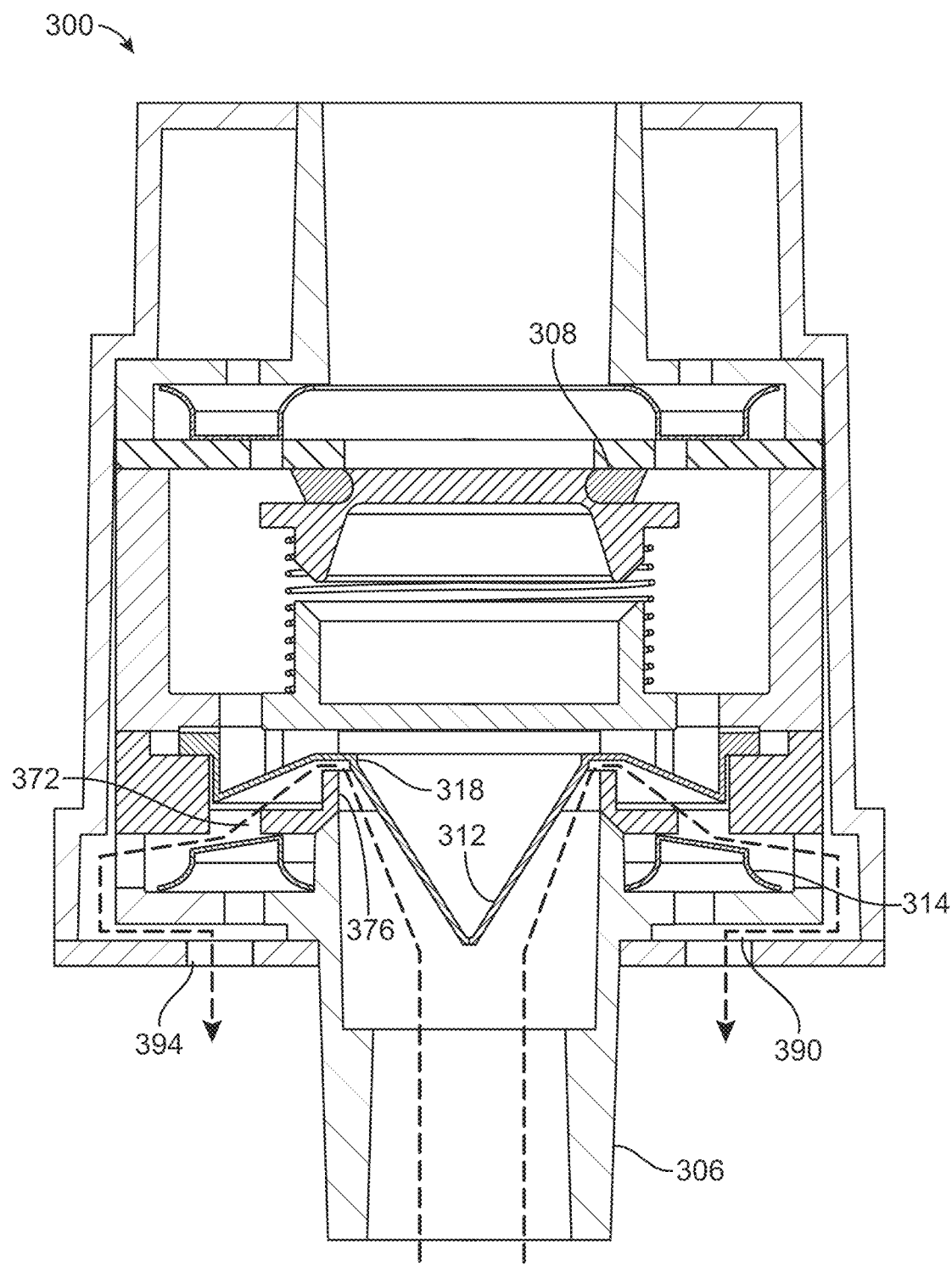
FIG. 3E illustrates airflow through the IRV of FIG. 3A during a chest compression phase of CPR or a patient expiration.

FIGS. 3C-3F illustrate the operation of the IRV 300 under different respiration conditions. As shown by the arrows of FIGS. 3C-3E, the flow paths of respiratory air during positive pressure ventilations, spontaneous inspiration, and expiration may be concentrically aligned about an axis of the IRV 300. The arrows in FIG. 3C illustrate airflow through the IRV 300 during delivery of a positive pressure ventilation. Positive pressure ventilations may be delivered using a manual and/or automated respirator that is coupled with the ventilation port 304. During ventilation, air is typically forced into the IRV 300 via the ventilation port 304 and forces the atmospheric diaphragm 310 to open. The air then enters the annular lumen 302 and apertures 338 before passing into an interior of one-way valve 312. The air then forces open the one-way valve 312 and is delivered to the patient's airway via the patient port 306. During positive pressure ventilations, the safety check valve 308 and exhalation valve 314 remain closed, such that all air delivered by the respirator is delivered to the patient. In some embodiments one-way valve 312 opens with each positive pressure breath and simultaneously blocks respiratory gases from exiting through the expiratory port 304. For example, the outer surface 318 of the one-way valve 312 may be against the valve seat 376 of the expiratory port plate 370 so as to occlude the apertures 372 from the respiratory gases, thereby closing off the expiratory flow path. In such configurations one-way valve 312 may preferably be designed as a fish-mouth or duck bill valve serving two functions: 1) to prevent backflow of gases and fluids from the lungs and 2) to occlude the expiratory port structure during a positive pressure breath.

In some cases, the patient may spontaneously inspire, creating a negative pressure within the chest that causes air to be drawn into the patient port 306 as demonstrated by the arrows in FIG. 3D. The negative pressure within the chest opens the one-way valve 312, and if the negative pressure is sufficiently low, the safety check valve 308 may be drawn downward against the spring force of spring 362. Air may then be drawn into the annular lumen 302 and apertures 338 from the ventilation port 304 via the central aperture 344. During spontaneous inspiration, the negative pressure within the chest maintains the exhalation valve 314 in a closed position and biases the outer surface 318 of the one-way valve against the valve seat 376. Atmospheric diaphragm 310 is also in a closed position during spontaneous inspiration. The configuration described above enables a patient to gasp and pull in air on their own, with the valve system properly opening without the use of any pressure sensors.

Rather, the cracking pressure, with a range from −5 to −20 cm H2O, and arrangement of the various valves enables this spontaneous inspiration. In alternative embodiments this range of cracking pressures may be adjustable by altering, for example, the spring tension within the safety check valve.

When the chest is compressed (manually and/or automatically) and/or the patient expires, respiratory gases flow from the patient and out through the IRV 300 as shown by the arrows in FIG. 3E. For example, expiratory gases pass through the patient port 306 and force the outer surface 318 of one-way valve 312 to move away from the valve seat 376 to provide access to the apertures 372. The expiratory gases may then force exhalation valve 314 to open and pass through the filter 390 and outer exhalation ports 394. Due to the direction of operation of the safety check valve 308 and one-way valve 312, these valves 308, 312 remain closed during patient expiration. This arrangement is particularly useful for patients that suffer from pulmonary edema, which may cause fluid to build up in the lungs that may be expired through the IRV 300. Due to the one-way valve arrangement of IRV 300, any fluids (expiratory gases and/or pulmonary edema fluid) is directed through the exhalation valve 314 and expelled via the outer exhalation ports 394, thereby preventing any pulmonary edema fluid from passing through and/or obstructing the proper operation of safety check 308 and one-way valve 312. Additionally, the valve arrangement of IRV 300 effectively separates the inspiratory flow from the expiratory flow such that expiratory gases will not be mixed with inspiratory gases. This enables the delivery of higher concentrations of oxygen to the patient during CPR, thereby allowing higher oxygenation levels within the patient's bloodstream and resulting in improved resuscitation outcomes.

Figure 3F:
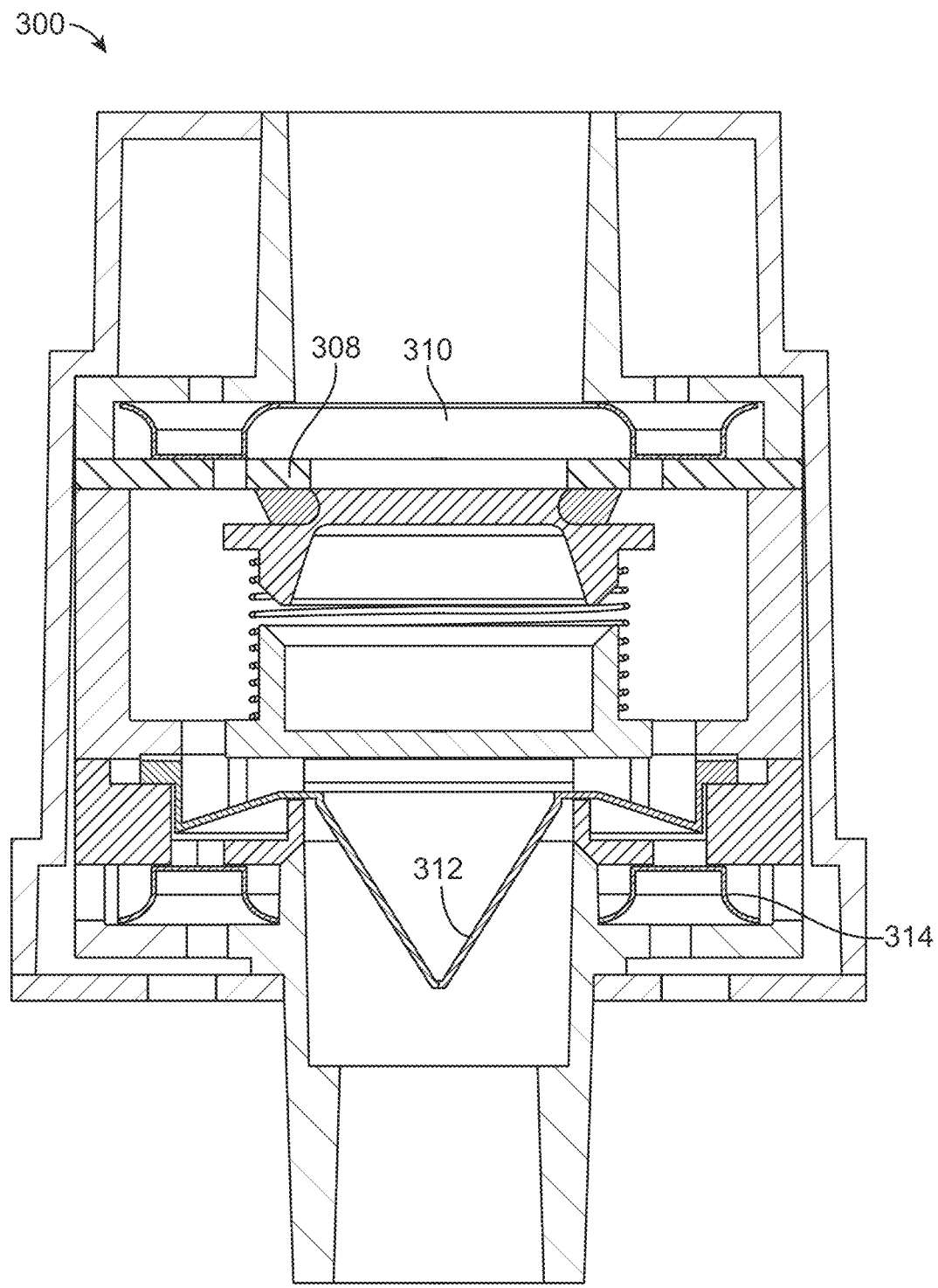
FIG. 3F illustrates a state of the IRV of FIG. 3A during a decompression phase of CPR.

During the decompression phase of CPR, the chest wall recoils as the rescuers hands are lifted. In the case of ACD-CPR, the chest is actively decompressed, such as by using a suction cup and/or adhesive to draw the chest upward. During this phase of CPR, a negative pressure is created within the chest (below the cracking pressure of the safety check valve 308). FIG. 3F illustrates the state of IRV 300 during the decompression phase of CPR. Here, the safety check valve 308, exhalation valve 314, and atmospheric diaphragm 310, are closed, thereby preventing respiratory gases from entering the patient. By preventing respiratory gases from entering the patient over multiple cycles of chest compressions and chest recoil, less and less air is present within the thorax, providing room for more and more blood to return to the heart during the chest wall recoil phase. This increases circulation to the coronary arteries and lowers intracranial pressure during the chest wall decompression phase, resulting in greater rates of successful resuscitation.

It is important to note that the drawings shown herein represent the potential path for gas exchange into and out of the patient but the dimensions in IRV 300 are representative but not exactly to scale and only one of a multitude of potential valve mechanisms (e.g. duck bill, ball valve, annular valve, circular valve, balloon valve, fish mouth, mushroom, disk valve, etc.) in shown in FIGS. 3A-3F.

In some embodiments, the IRV 300 may be described in terms of a number of regions. For example, IRV 300 may include an upper region, a lower region, and an expiratory region. The diaphragm 310 and/or safety check valve 308 may separate the upper region from the lower region such that the upper region may include any portions of the IRV included in the inspiratory flow path that are on a ventilation port side of the diaphragm 310 and/or safety check valve 308, including ventilation port 304. The lower region of the IRV 300 may include all portions of the IRV 300 that are included in the inspiratory flow path that are on a patient port side of the diaphragm 310 and/or safety check valve 308, including annular lumen 302, apertures 338, and patient port 306. The expiratory region may include all portions of the IRV 300 that are included in the expiratory flow path other than the ventilation port 304. For example, the expiratory region may include the gap between outer surface 318 and valve seat 376, apertures 372, filter 390, and outer exhalation ports 304. The lower region and upper region may be separated by two valves (which may be considered a singular non-rebreather valve in some embodiments). For example, the one-way valve 312 may be disposed between the lower region and upper region and may close to prevent all expiratory fluids from flowing to the upstream region when the pressure in the thorax is greater than atmospheric pressure. The interface between the outer surface 118 and valve seat 376 may close to occlude the expiratory region when pressure in the patient port 304 is below atmospheric pressure and may open to enable expiratory fluids to be expelled from the IRV 300 when pressure in the patient port 304 is above atmospheric pressure.

Figure 4:
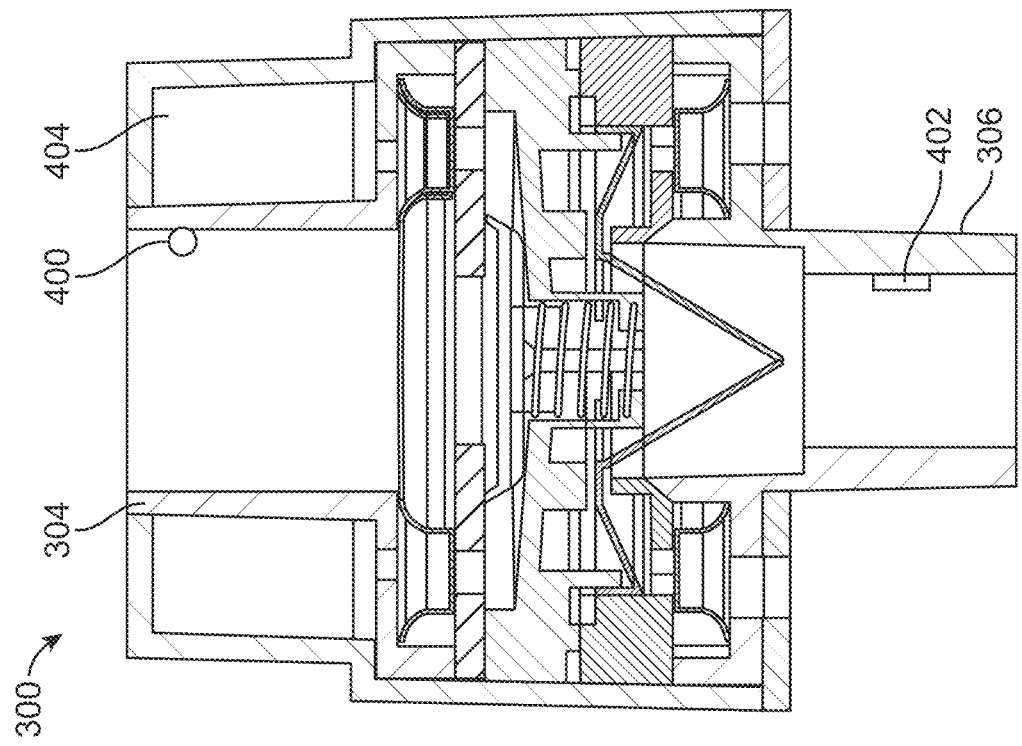
FIG. 4 illustrates sensors arranged within the IRV of FIG. 3A.

In some embodiments, the IRV 300 one or more sensors. For example, IRV 300 may include a sensor 400 positioned within the ventilation port 304 and/or sensor 402 positioned within the patient port 306 as shown in FIG. 4. For example, sensor 400 and/or 402 may be physiological sensors, such as pressure sensors and/or flow sensors. Measurements from sensor 400 and/or 402 may be used to determine a chest compression/decompression cycle. Data from the sensors 400, 402 may be transmitted to a ventilation device and/or a chest compression device using a communications interface that includes one or more wired and/or wireless connections, including Bluetooth connections. The compression/decompression cycle data may be used by the ventilation device and/or chest compression device to synchronize delivery of positive pressure breaths with the compression/decompression cycle. One or more indicator mechanisms, such as lights and/or display screens may be provided on or within the IRV 300. For example, one or more lights 404 may be disposed on or within housing 320. Lights 404 may indicate various parameters, such as a phase of a ventilation cycle, timing of a ventilation rate, and/or a particular pressure level within the IRV 300.

Figure 5:
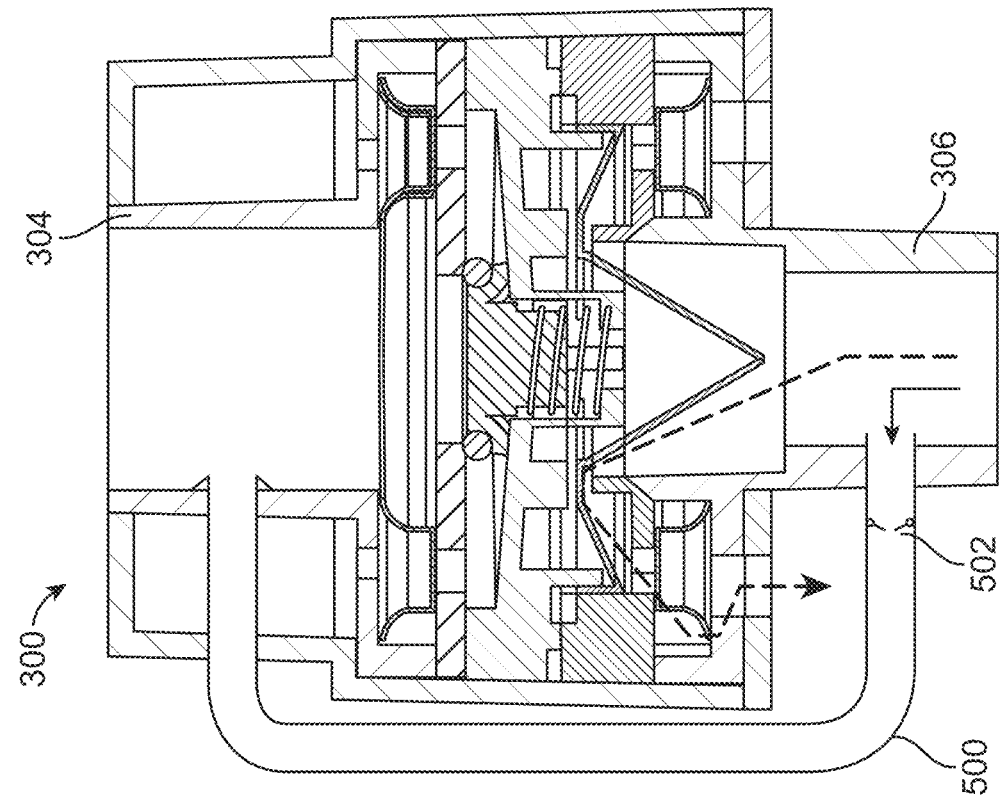
FIG. 5 illustrates a sampling tube incorporated in the IRV of FIG. 3A.

In some embodiments, the IRV 300 may be configured to sense pressures within the thorax. For example, IRV 300 may include a lumen 500 that fluidly couples and extends directly between the patient port 306 and ventilation port 304 as shown in FIG. 5. A one-way valve 502 may be included within the lumen 500. With each chest compression, some of the expiratory flow may pass through one-way valve 502 (while a majority of the expiratory flow passes through the exhalation valve 314). In an alternative embodiment, lumen 500 may be sealed at the patient port and ventilation port with a pressure sensitive material, e.g. a membrane, such that pressures can be readily transmitted but fluids and/or gases cannot be transmitted from the patient port to the ventilation port. In some such embodiments, the sealed off portion may be filled with a fluid or gas to facilitate pressure transduction. This allows a pressure within the chest to be sensed using a sensor within the ventilation port 304 for synchronization of positive pressure breath delivery as described above. In some embodiments IRV 300 may be coupled to a ventilator circuit and the lumen at the patient port can connected to a sensor either in the patient port region or within the ventilator circuit. In such embodiments, IRV 300 may be reversibly or irreversibly coupled to the ventilation source or ventilation source circuit.

EXAMPLE

Figure 6:
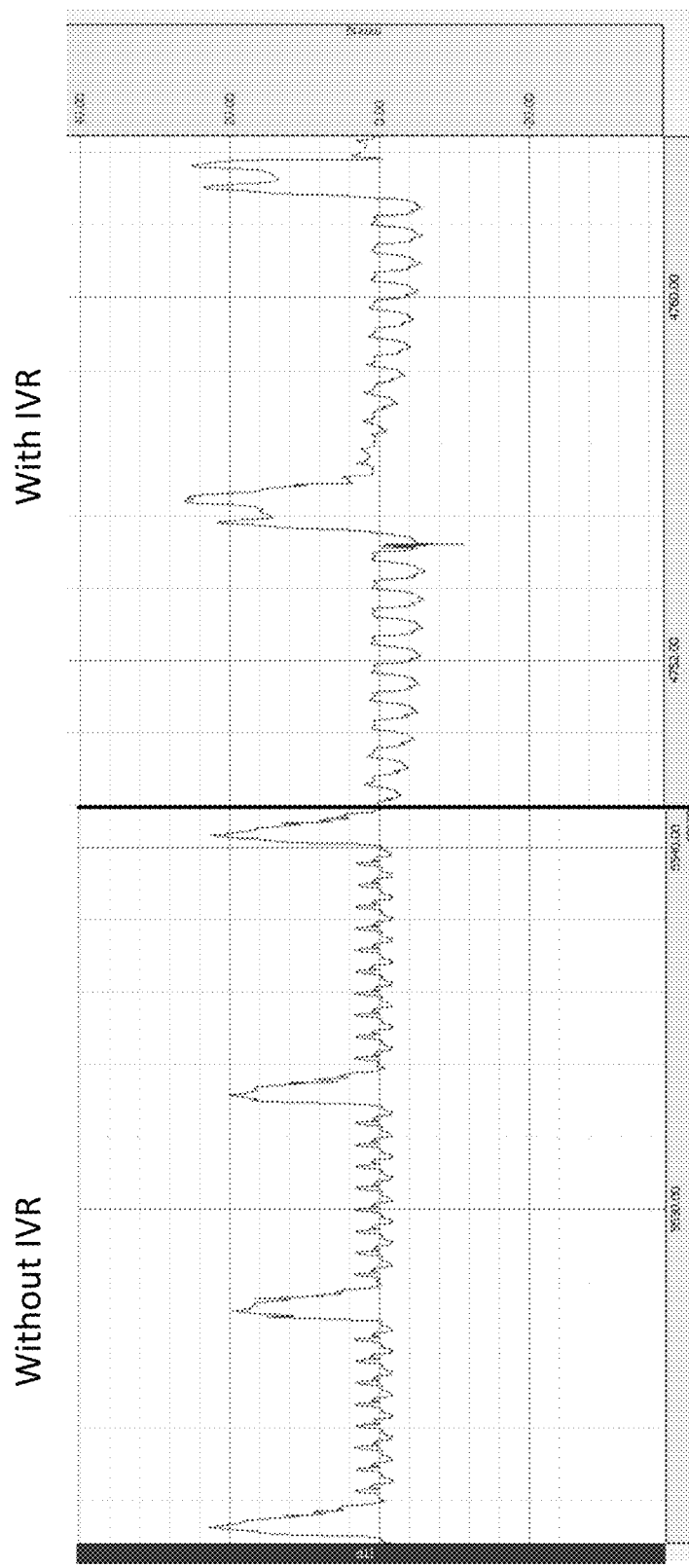
FIG. 6 is a graph showing airway pressure and intrathoracic pressure during CPR with and without an IRV.

In an anesthetized pig, CPR was performed with an automated device that provides for compression and active decompression. A functional IRV, as described in this patent, that includes an inspiratory port and a separate expiratory port (similar to IRV 300), was attached to the endotracheal tube and pressures were measured with a pressure transducer at the level of the patient port. With each positive pressure breath airway pressures increased to approximately 20 mmHg and during each decompression phase they decreased to approximately −5 mmHg as illustrated in FIG. 6.

The IRVs described herein may be used in conjunction with physiological sensors, air flow sensors, pressure transducers, timing and/or status lights, impedance sensors to detect air/blood ratio in the thorax, and/or a controller or other interface of a CPR device, ventilator, and/or AED to provide feedback related to how to perform CPR, deliver positive pressure ventilations, and/or deliver shocks to a patient. Further, information from and additional control of such sensors, transducers, lights, detectors, and other controllers may be transferred by a direct wire connection, blue tooth, and other non-hardwired means of communication between devices. Additionally, in some embodiments, the one-way valve 108, vacuum valve 208, and/or safety check valve 308 may be coupled with a 'gasping gauge' or sensor that detects when the respective valve has opened. The sensor may trigger the activation of a light and/or sound that alerts a rescuer that the patient is trying to breathe.

The methods, systems, and devices discussed above are examples. Some embodiments were described as processes depicted as flow diagrams or block diagrams. Although each may describe the operations as a sequential process, many of the operations can be performed in parallel or concurrently. In addition, the order of the operations may be rearranged. A process may have additional steps not included in the figure. It will be further appreciated that all testing methods described here may be based on the testing standards in use at the time of filing or those developed after filing.

It should be noted that the systems and devices discussed above are intended merely to be examples. It must be stressed that various embodiments may omit, substitute, or add various procedures or components as appropriate. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known structures and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

What is claimed is:

1. An inspiratory resistor valve system (IRV) to regulate intrathoracic pressure during positive pressure breathing, spontaneous inspirations, and CPR, comprising:
   an inspiratory port;
   a patient port;
   a separate expiratory port;
   a first atmospheric pressure sensitive valve that permits inspiratory flow through the inspiratory port when open;
   a second atmospheric pressure sensitive valve that permits expiratory flow through the expiratory port, wherein one or both of the first atmospheric pressure sensitive valve and the second atmospheric pressure sensitive valve isolate the expiratory port and the inspiratory port from one another; and a safety check valve having a cracking pressure of between about −5 and −20 mm Hg, the safety check valve being configured to open to permit inspiratory flow to flow from the inspiratory port through the patient port during spontaneous inspiration of a patient while the first atmospheric pressure sensitive valve remains closed.

2. The inspiratory resistor valve system (IRV) to regulate intrathoracic pressure during positive pressure breathing, spontaneous inspirations, and CPR of claim 1, wherein:
the first atmospheric pressure sensitive valve, the second atmospheric pressure sensitive valve, and the safety check valve are concentrically arranged.

3. The inspiratory resistor valve system (IRV) to regulate intrathoracic pressure during positive pressure breathing, spontaneous inspirations, and CPR of claim 1, wherein:
the first atmospheric pressure sensitive valve, the second atmospheric pressure sensitive valve, and the safety check valve are concentrically arranged with the patient port.

4. The inspiratory resistor valve system (IRV) to regulate intrathoracic pressure during positive pressure breathing, spontaneous inspirations, and CPR of claim 1, wherein:
the first atmospheric pressure sensitive valve and the second atmospheric pressure sensitive valve occlude the expiratory port during positive pressure breath delivery and occlude the inspiratory port and open the expiratory port to enable egress of respiratory gases from a patient's lung during expiration or chest compressions.

5. The inspiratory resistor valve system (IRV) to regulate intrathoracic pressure during positive pressure breathing, spontaneous inspirations, and CPR of claim 1, wherein:
between 2 and 10 cm of water of expiratory resistance is provided by one or both of a filter interfaced with the expiratory port and a third pressure sensitive valve.

6. The inspiratory resistor valve system (IRV) to regulate intrathoracic pressure during positive pressure breathing, spontaneous inspirations, and CPR of claim 1, wherein:
each of the first atmospheric pressure sensitive valve, the second atmospheric pressure sensitive valve, and the safety check valve comprise one-way valves selected from a group consisting of: a duckbill valve, a ball valve, an annular valve, a circular valve, a butterfly valve, a check valve, a balloon valve, a mushroom valve, a fish mouth valve, and a disk valve.

7. The inspiratory resistor valve system (IRV) to regulate intrathoracic pressure during positive pressure breathing, spontaneous inspirations, and CPR of claim 1, wherein:
the second atmospheric pressure sensitive valve operates as a non-rebreather valve that enables substantially resistance-free positive pressure ventilation from the inspiratory port to the patient port.

8. An inspiratory resistor valve system (IRV) to regulate intrathoracic pressure during positive pressure breathing, spontaneous inspirations, and CPR, comprising:
an inspiratory port;
a patient port;
a separate expiratory port;
a non-rebreather valve that moves between a first position and a second position, wherein:
in the first position, the non-rebreather valve enables expiratory fluids to be expelled through the expiratory port and prevents the expiratory fluids from flowing to the inspiratory port when the pressure in the patient port is greater than atmospheric pressure; and
in the second position enables inspiratory flow to pass into the patient port while occluding the expiratory port when the pressure in the patient port is less than atmospheric pressure;
an atmospheric pressure sensitive valve that permits inspiratory flow through the inspiratory port when open; and
a safety check valve having a cracking pressure of between about −5 and −20 cm $H_2O$, the safety check valve being configured to open to permit inspiratory flow during spontaneous inspiration of a patient while the atmospheric pressure sensitive valve remains closed.

9. The inspiratory resistor valve system (IRV) to regulate intrathoracic pressure during positive pressure breathing, spontaneous inspirations, and CPR of claim 8, wherein:
in the first position, a portion of the non-rebreather valve is spaced apart from a valve seat formed proximate the patient port, thereby enabling expiratory gases to pass through a gap formed between the portion of the non-rebreather valve and the valve seat; and
in the second position, the portion of the non-rebreather valve is in contact with the valve seat.

10. The inspiratory resistor valve system (IRV) to regulate intrathoracic pressure during positive pressure breathing, spontaneous inspirations, and CPR of claim 8, wherein:
in the first position, an inspiratory portion of the non-rebreather valve is closed, thereby preventing expiratory gases from passing into the inspiratory port; and
in the second position, the inspiratory portion of the non-rebreather valve is open to permit inspiratory gases to enter the patient port.

11. The inspiratory resistor valve system (IRV) to regulate intrathoracic pressure during positive pressure breathing, spontaneous inspirations, and CPR of claim 10, wherein:
the inspiratory portion comprises a fish-mouth valve or a duck bill valve.

12. The inspiratory resistor valve system (IRV) to regulate intrathoracic pressure during positive pressure breathing, spontaneous inspirations, and CPR of claim 8, further comprising:
a filter interfaced with the expiratory port.

13. An inspiratory resistor valve system (IRV) to regulate intrathoracic pressure during positive pressure breathing, spontaneous inspirations, and CPR, comprising:
an inspiratory port;
a patient port;
a separate expiratory port;
a first atmospheric pressure sensitive valve that permits inspiratory flow through the inspiratory port when open;
a second atmospheric pressure sensitive valve that permits expiratory flow through the expiratory port, wherein one or both of the first atmospheric pressure sensitive valve and the second atmospheric pressure sensitive valve isolate the expiratory port and the inspiratory port from one another; and
a safety check valve having a cracking pressure of between about −5 and −20 mm Hg, the safety check valve being configured to open to permit inspiratory flow during spontaneous inspiration of a patient while the first atmospheric pressure sensitive valve remains closed.

14. The inspiratory resistor valve system (IRV) to regulate intrathoracic pressure during positive pressure breathing, spontaneous inspirations, and CPR of claim 13, wherein:

when open, the safety check valve permits inspiratory flow to be introduced to the patient port via the inspiratory port.

15. The inspiratory resistor valve system (IRV) to regulate intrathoracic pressure during positive pressure breathing, spontaneous inspirations, and CPR of claim 13, further comprising:
at least one spontaneous inspiration port that is fluidly coupled with an outside environment, wherein when open, the safety check valve permits inspiratory flow to be introduced to the patient port via the at least one spontaneous inspiration port.

16. The inspiratory resistor valve system (IRV) to regulate intrathoracic pressure during positive pressure breathing, spontaneous inspirations, and CPR of claim 13, wherein:
inspiratory flow is introduced to the patient port via the expiratory port during spontaneous inspiration of the patient.

17. The inspiratory resistor valve system (IRV) to regulate intrathoracic pressure during positive pressure breathing, spontaneous inspirations, and CPR of claim 13, wherein:
the safety check valve is biased in a closed position by a spring.

18. The inspiratory resistor valve system (IRV) to regulate intrathoracic pressure during positive pressure breathing, spontaneous inspirations, and CPR of claim 13, further comprising:
a physiological sensor disposed in one or both of the inspiratory port and the patient port.

* * * * *